US007915227B2

(12) United States Patent
Veldman et al.

(10) Patent No.: US 7,915,227 B2
(45) Date of Patent: Mar. 29, 2011

(54) PHARMACEUTICAL FORMULATIONS EMPLOYING SHORT-CHAIN SPHINGOLIPIDS AND THEIR USE

(75) Inventors: Robert J. Veldman, Huizen (NL); Wim J. Van Blitterswijk, Westzaan (NL); Marcel Verheij, Lisse (NL); Gerben A. Koning, Houten (NL)

(73) Assignee: Het Nederlands Kanker Instituut, Amsterdam (NL)

( * ) Notice: Subject to any disclaimer, the term of this patent is extended or adjusted under 35 U.S.C. 154(b) by 1158 days.

(21) Appl. No.: 10/579,230

(22) PCT Filed: Nov. 11, 2004

(86) PCT No.: PCT/IB2004/003886
§ 371 (c)(1),
(2), (4) Date: Sep. 28, 2006

(87) PCT Pub. No.: WO2005/046637
PCT Pub. Date: May 26, 2005

(65) Prior Publication Data
US 2007/0082855 A1 Apr. 12, 2007

(30) Foreign Application Priority Data

Nov. 14, 2003 (GB) .................................. 0326642.6
Nov. 17, 2003 (GB) .................................. 0326759.8

(51) Int. Cl.
*A61K 31/70* (2006.01)
*A61K 31/704* (2006.01)
*A61K 31/7008* (2006.01)
*A61K 31/685* (2006.01)
*C07H 15/00* (2006.01)

(52) U.S. Cl. ................ 514/25; 514/23; 514/53; 514/34; 514/78; 536/17.9; 536/4.1; 536/53

(58) Field of Classification Search ................... 514/25, 514/23, 53, 34, 78; 536/17.9, 4.1, 53
See application file for complete search history.

(56) References Cited

U.S. PATENT DOCUMENTS

| 4,416,872 | A |   | 11/1983 | Alving et al. |   |
|---|---|---|---|---|---|
| 5,013,556 | A |   | 5/1991 | Woodle et al. |   |
| 5,213,804 | A |   | 5/1993 | Martin et al. |   |
| 5,395,619 | A |   | 3/1995 | Zalipsky et al. |   |
| 5,527,528 | A |   | 6/1996 | Allen et al. |   |
| 5,800,833 | A |   | 9/1998 | Hope et al. |   |
| 5,936,076 | A | * | 8/1999 | Higa et al. | .................. 536/17.9 |
| 6,054,433 | A | * | 4/2000 | Elias et al. | ....................... 514/25 |
| 2002/0119990 | A1 |   | 8/2002 | Madden |   |

FOREIGN PATENT DOCUMENTS

| EP | 0 896 816 |   | 2/1999 |
|---|---|---|---|
| EP | 0 896 816 | A1 | 2/1999 |
| JP | 8-034746 |   | 2/1996 |
| WO | WO 88/01171 |   | 2/1988 |
| WO | WO 99/41266 |   | 8/1999 |
| WO | 02/02077 | A2 | 1/2002 |
| WO | WO 02/02077 |   | 1/2002 |

OTHER PUBLICATIONS

Slotte et al. (Biochemistry (1993), 32(31), 7886-92) (Abstract sent).*
Futerman et al.(Methods in Enzymology (1992), 209(Phospholipid Biosynth.), 437-46) (Abstract sent).*
Abe et al. (European Journal of Biochemistry (1992), 210(3), 765-73).*
Abraham SA, et al, 2002, "Formation of transition metal-doxorubicin complexes inside liposomes," *Biochim. Biophys. Acta.*, vol. 1565(1), pp. 41-54.
Bai J, et al, 1997, "Measurement of spontaneous transfer and transbilayer movement of BODIPY-labeled lipids in lipid vesicles," *Biochemistry*, vol. 36, pp. 8840-8848.
Bligh EJ, et al, 1959, "A rapid method of total lipid extraction and purification," *Can. J. Biochem. Physiol.*, vol. 37, pp. 911-917.
Carmichael J, et al, 1987, "Evaluation of a tetrazolium-based semiautomated colorimetric assay: assessment of chemosensitivity testing," *Cancer Res.*, vol. 47, pp. 936-942.
Cheung BC, et al, 1998, "Loading of doxorubicin into liposomes by forming Mn2+-drug complexes," *Biochim. Biophys. Acta.*, vol. 1414(1-2), pp. 205-216.
Druckmann S, et al, 1989, "Separation of liposome-associated doxorubicin from non-liposome-associated doxorubicin in human plasma: implications for pharmacokinetic studies," *Biochim. Biophys. Acta*, vol. 980, pp. 381-384.
Everts M, et al, 2003, "In vitro cellular handling and in vivo targeting of E-selectin-directed immunoconjugates and immunoliposomes used for drug delivery to inflamed endothelium," *Pharm. Res.*, vol. 20, pp. 64-72.
Gabizon A, 2001, "Pegylated liposomal doxorubicin: metamorphosis of an old drug into a new form of chemotherapy," *Cancer Inv.*, vol. 19, pp. 424-436.
Gabizon A, et al, 1996, "Liposome longevity and stability in circulation: effects on the in vivo delivery to tumors and therapeutic efficacy of encapsulated anthracyclines," *J. Drug Target*, vol. 3, pp. 391-398.
Ghidoni R, et al, 1999, "Use of sphingolipid analogs: benefits and risks," *Biochim. Biophys. Acta*, vol. 1439, pp. 17-39.
Haran G, et al Y, 1993, "Transmembrane ammonium sulphate gradients in liposomes produce efficient and stable entrapment of amphipathic weak bases," *Biochim. Biophys. Acta*, vol. 1151, pp. 201-215.
Harasym TO, et al, 1997, "Intratumor distribution of doxorubicin following i.v. administration of drug encapsulated in egg phosphatidylcholine/ cholesterol liposomes," *Cancer Chemother. Pharmacol.*, vol. 40, pp. 309-317.
Heijn M, et al, 1999, "Cellular membrane permeability of anthracyclines does not correlate with their delivery in a tissue-isolated tumor," *Cancer Res.*, vol. 59, pp. 4458-4463.

(Continued)

*Primary Examiner* — Shaojia Anna Jiang
*Assistant Examiner* — Michael C Henry
(74) *Attorney, Agent, or Firm* — Nixon & Vanderhye P.C.

(57) ABSTRACT

Pharmaceutical formulations containing (i) an amphiphilic drug and (ii) a short-chain sphingolipid are described and provided herein along with methods of making and using same.

55 Claims, 4 Drawing Sheets

OTHER PUBLICATIONS

Horowitz AT, et al, 1992, "In vitro cytotoxicity of liposome-encapsulated doxrubicin: dependence on liposome composition and drug release," *Biochim. Biophys. Acta*, vol. 1109, pp. 203-209.

Jeckel D, et al, 1993, "Truncated ceramide analogs as probes for sphingolipid biosynthesis and transport," *Adv. Lipid Res.*, vol. 26, pp. 143-160.

Koning GA, et al, 1999, "Antiproliferative effect of immunoliposomes containing 5-fluorodeoxyuridine-dipalmitate on colon cancer cells," *Br. J. Cancer*, vol. 80, pp. 1718-1725.

Koning GA, et al, 2003, "Interaction of differently designed immunoliposomes with colon cancer cells and Kupffer Cells. An in vitro comparison," *Pharm. Res.*, vol. 20, pp. 1249-1257.

Koning, G.A., et al, 2003, "Short-chain liposomal sphingolipids potentiate in vitro doxorubicin cytotoxicity by enhancing its cellualr influx," Conference Abstract for Liposome Advances: Progress in Drug and Vaccine Delivery, Dec. 15-19, 2003, London, UK.

Lasic DD, et al, 1995, "Transmembrane gradient driven phase transitions within vesicles: lessons for drug delivery," *Biochim. Biophys. Acta.*, vol. 1239(2), pp. 145-156.

Lothstein L, et al, 2001, "Anthracyclin drug targeting: cytoplasmic versus nuclear—a fork in the road," *Drug Res. Updates*, vol. 4, pp. 169-177.

Mabrey, S., et al, 1978, "High-sensitivity scanning calorimetric study of mixtures of cholesterol with dimyristoyl- and dipalmitoylphosphatidylcholines", *Biochem.*, vol. 17, pp. 2464-2468.

Martin, F.J., 1990, "Pharmaceutical Manufacturing of Liposomes", *Specialized Drug Delivery Systems—Manufacturing and Production Technology*, pp. 267-316.

Mayer, L.D., et al, 1986, "Uptake of adriamycin into large unilamellar vesicles in response to a pH gradient", *Biochim. Biophys. Acta*, vol. 857, pp. 123-126.

Mayer, L.D., et al., 1989, "Influence of vesicle size, lipid composition, and drug-to-lipid ratio on the biological activity of liposomal doxorubicin in Mice", *Cancer Res.*, vol. 49, pp. 5922-5930.

Olson, F., et al, 1979, "Preparation of liposomes of defined size distribution by extrusion through polycarbonate membranes", *Biochim. Biophys. Acta*, vol. 557, pp. 9-23.

Pan, XQ, et al, 2003, "Antitumor activity of folate receptor-targeted liposomal doxorubcin in a KB oral carcinoma murine xenograft model," *Pharm. Res.*, vol. 20, pp. 417-422.

Park, JW, et al, 2002, "Anti-HER2 immunoliposomes: enhanced efficacy attributable to targeted delivery," *Clin. Cancer Res.*, vol. 8, pp. 1172-1181.

Robert J, et al, 1993, "Pharmacokinetics and metabolism of anthracyclines," in *Cancer Surveys*, vol. 17, pp. 219-252.

Rouser G, et al, 1970, "Two-dimensional thin layer chromatographic separation of polar lipids and determination of phospholipids by phosphorus analysis of spots," *Lipids*, vol. 5, pp. 494-496.

Sillence, D.J., et al., 2000, "Assay for the transbilayer distribution of glycolipids: selective oxidation of glucosylceramide to glucuronylceramide by TEMPO nitroxyl radicals", *Journal of Lipid Research*, vol. 41, pp. 1252-1260.

Smith PK, et al, 1985, "Measurement of protein using bicinchoninic acid," *Anal. Chem.*, vol. 150, pp. 76-85.

Speth PA, et al, 1988, "In vivo cellular adriamycin concentrations related to growth inhibition of normal and leukemic human bone marrow cells," *Eur. J. Cancer Clin. Oncol.*, vol. 24, pp. 667-674.

Storm G, et al, 1985, "The interaction of cytostatic drugs with adsorbents in aqueous media. The potential implications for liposome preparation", *Biochim. Biophys. Acta*, vol. 818, pp. 341-351.

Szoka, F., Jr., et al, 1980, "Comparative properties and methods of preparation of lipid vesicles (liposomes)", *Ann. Rev. Biophys. Biogen.*, vol. 9, p. 457.

Tardi PG, et al, 1996, "Liposomal doxorubicin," *J. Drug Target*, vol. 4, pp. 129-140.

Tsong, T.Y., 1975, "Effect of phase transition on the kinetics of dye transport in phospholipid bilayer structures", *Biochem.*, vol. 14, pp. 5409-5414; pp. 5415-5417.

Tubaro, E., et al, 1995, "Effect of a new de-N-acetyl-lysoglycosphingolipid on some tumour models," *European Journal of Pharrnacology*, vol. 294, pp. 555-563.

Uster PS, et al, 1996, "Insertion of poly(ethylene glycol) derivatized phospholipid into pre-fromed liposomes results in prolonged in vivo circulation time," *FEBS Lett.*, vol. 386, pp. 243-246.

Vaage J, et al, 1992, "Therapy of primary and metastatic mouse mammary carcinomas with doxorubicin encapsulated in long circulating liposomes," *Int. J .Cancer*, vol. 51, pp. 942-948.

Veldman, R.J., et al, 2004, "N-hexanoyl-sphingomyelin potentiates in vitro doxorubicin cytotoxicity by enhancing its cellular influx," *British Journal of Cancer*, vol. 90, pp. 917-925.

Veldman, R.J., et al., 1999, "Inhibition of P-glycoprotein activity and chemosensitization of multidrug-resistant ovarian carcinoma 2780AD cells by hexanoylglucosylceramide", *Biochemical & Biophysical Research Communications*, vol. 266, pp. 492-496.

Verheij, M., et al, 2003, "N-hexanoyl-sphingomyelin potentiates in vitro doxorubicin cytotoxicity by enhancing its cellular influx," Conference Abstract #C228 for AACR-NCI-EORTC International Conference on Molecular Targets and Cancer Therapeutics, Nov. 17-21, 2003, Boston, MA, USA.

Washington N, et al, 2001, "Cell membranes, epithelial barriers and drug absorption," in *Physiological Pharmaceutics: Barriers to Drug Absorption*, pp. 1-18, (publishers: Taylor and Francis: London).

Weiss RB, 1992, "The anthracyclines: will we ever find a better doxorubicin?", *Sem. Oncol.*, vol. 19, pp. 670-686.

Yuan F, et al, 1994, "Microvascular permeability and interstitial penetration of sterically stabilized (stealth) liposomes in a human tumor xenograft," *Cancer Res.*, vol. 54, pp. 3352-3356.

Zagotto G, et al, 2001, "Anthracyclins: recent developments in their separation and quantitation," *J. Chromat. B*, vol. 764, pp. 161-171.

International Preliminary Report on Patentability (IPRP) of PCT/GB2004/003886.

International Search Report (ISR) of PCT/GB2004/003886.

Search Report of GB 0326642.6.

International Search Report of PCT/B32004/003886, mailed May 11, 2005.

Sillence et al; "Assay for the transbilayer distribution of blycolipids: selective oxidation of glucosylceramide to glucuronylceramide by TEMPO nitroxyl radicals", Journal of Lipid Research, vol. 41, 2000, pp. 1252-1260, XP-002324330.

Veldman et al., "Inhibition of P-Glycoprotein Activity and Chemosensitization of Multidrug-Resistant Ovarian Carcinoma 2780AD Cells by Hexanoylglucosylceramide", Biochemical and Biophysical Research Communications, vol. 266, No. 2, 1999, pp. 492-496, XP-002324331.

* cited by examiner

PHARMACEUTICAL FORMULATIONS EMPLOYING SHORT-CHAIN SPHINGOLIPIDS AND THEIR USE

This application is the US national phase of international application PCT/IB2004/003886, filed 11 Nov. 2004, which designated the U.S. and claims priority of GB 0326642.6, filed 14 Nov. 2003, and GB 0326759.8, filed 17 Nov. 2003, the entire contents of each of which are hereby incorporated by reference.

RELATED APPLICATIONS

This application is related to United Kingdom patent application GB 0326642.6 filed 14 Nov. 2003 and United Kingdom patent application GB 0326759.8 filed 17 Nov. 2003, the contents of both of which are incorporated herein by reference in their entirety.

TECHNICAL FIELD

This invention pertains generally to the field of pharmaceuticals and pharmaceutical formulations, and more specifically to the co-formulation of known drugs (e.g., amphiphilic drugs) (e.g., anthracyclines) (e.g., doxorubicin) with certain short-chain sphingolipids (e.g., short-chain glycosphingolipids and short-chain sphingomyelins) (e.g., N-octanoyl-glucosylceramide, referred to as $C_8$-GlcCer) (e.g., N-hexanoyl-sphingomyelin, referred to herein as $C_6$-SM), for improved drug delivery and efficacy.

BACKGROUND

Throughout this specification, including any claims which follow, unless the context requires otherwise, the word "comprise," and variations such as "comprises" and "comprising," will be understood to imply the inclusion of a stated integer or step or group of integers or steps, but not the exclusion of any other integer or step or group of integers or steps.

It must be noted that, as used in the specification and any appended claims, the singular forms "a," "an," and "the" include plural referents unless the context clearly dictates otherwise. Thus, for example, reference to "a pharmaceutical carrier" includes mixtures of two or more such carriers, and the like.

Ranges are often expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

Anthracyclines: Doxorubicin

The anthracycline doxorubicin has been in clinical use for several decades, and is still among the most widely used chemotherapeutic agents for treatment of a variety of neoplasms (see, e.g., Weiss, 1992; Zagotto et al., 2001; Lothstein et al., 2001).

Doxorubicin has several cytotoxic actions. It binds to DNA and inhibits both DNA and RNA synthesis, but its main cytotoxic action appears to be mediated through an effect on topoisomerase II (a DNA gyrase), the activity of which is markedly increased in proliferating cells. The significance of the enzyme lies in the fact that during replication of the DNA helix, reversible swivelling needs to take place around the replication fork in order to prevent the daughter DNA molecule becoming inextricably entangled during mitotic segregation. The swivel is produced by topoisomerase II, which nicks both DNA strands and subsequently reseals the breaks. Doxorubicin intercalates in the DNA and its effect is, in essence, to stabilise the DNA-topoisomerase II complex after the strands have been nicked, thus causing the process to seize up at this point.

Liposomal Delivery

Despite many years of research in developing new and better anthracyclines, little or no change in the molecular structure of doxorubicin made it to the clinics. However, with the development of liposomal formulations, its delivery form underwent a major improvement (see, e.g., Tardi et al., 1996; Gabizon, 2001). Compared to systemic application of doxorubicin in its free form, liposomal doxorubicin exhibits significant advantages, as for example reduced acute and chronic toxicities. Improved loading procedures, resulting in high doxorubicin packing efficiencies, further increased the therapeutic index of encapsulated doxorubicin (see, e.g., Horowitz et al., 1992; Haran et al., 1993). Another major step forward was the development of polyethyleneglycol (PEG)-coated liposomes. This coating prevents opsonization and reduces the uptake by macrophages from the reticulo-endothelial system, in turn resulting in prolonged circulation times, as compared to free doxorubicin or to non-coated liposomes (see, e.g., Vaage et al., 1992; Robert and Gianni, 1993; Gabizon et al., 1996; Uster et al., 1996). PEG-liposome-encapsulated doxorubicin (commercially available as Caelyx® and Doxil®) is now in routine clinical use, and innovations such as the coupling of targeting-enhancing features (e.g., tumor cell specific antibodies or ligands) will further enhance its therapeutic value (see, e.g., Park et al., 2002; Pan et al., 2003; Koning et al., 1999; Koning et al., 2003).

Both Caelyx® and Doxil® consist of: doxorubicin hydrochloride (2 mg/mL); N-(carbonyl-methoxypolyethylene glycol 2000)-1,2-distearoyl-sn-glycero-3-phosphoethanolamine sodium salt (MPEG2000-DSPE) (3.19 mg/mL); fully hydrogenated soy phosphatidylcholine (HSPC) (9.58 mg/mL); cholesterol (3.19 mg/mL); ammonium sulfate (~2 mg/mL); histidine (as a buffer); hydrochloric acid and/or sodium hydroxide (for pH control); sucrose (to maintain isotonicity); and water-for-injection.

The endothelial lining of healthy blood vessels effectively prevents escape of liposomes from the circulation. In contrast, angiogenesis-associated vascular abnormalities of many solid tumors, do allow extravasation of long-circulating PEG-liposomes into the tumor stroma (see, e.g., Yuan et al., 1994). Despite this tumor-specific accumulation, liposomes are, however, not taken up by tumor cells. Instead, doxorubicin is gradually released into the interstitial space (see, e.g., Horowitz et al., 1992; Harasym et al., 1997). Given the intracellular localization of its molecular targets, sufficient cellular uptake of doxorubicin is required for its action (see, e.g., Speth et al., 1988; Lothstein et al., 2001). However, since doxorubicin does not possess the optimal degree of lipophilicity for efficient plasma membrane traversal, this might be a limiting factor for its efficacy (see, e.g., Heijn et al., 1999; Washington et al., 2001).

Improved Liposomal Delivery

The inventors have demonstrated that the cellular uptake of free doxorubicin, and with that its cytotoxic action, is greatly enhanced by co-administration of the short-chain sphingolipid analogue N-hexanoyl-sphingomyelin (referred to herein as "$C_6$-SM"). Due to a truncated acyl-chain (attached to the amino group at the second carbon position of sphingosine), this lipid spontaneously inserts into lipid bilayers, and exchanges easily between membranes (see, e.g., Jeckel and Wieland, 1993; Ghidoni et al., 1999).

Despite the promising results obtained in vitro, several problems are to be expected when doxorubicin and the lipid analogue are co-administered separately, without any physical (e.g., liposomal) binding, in vivo, including: (1) For intravenous application of lipid solutions toxic solvents, such as ethanol, are required. (2) Lipids typically show poor plasma solubility, and might form undesired deposits on vessel walls. (3) Due to their high affinity for serum components, such as albumin and apolipoproteins, large amounts of lipid might be needed to obtain the desired effect. (4) Doxorubicin and the lipid analogue will most likely exhibit differences in biodistribution, and will thus not be delivered at the same site at the same time, which is a prerequisite for the drug-uptake enhancing effect.

The inventors have also demonstrated in vitro that liposomal anthracycline (for example, doxorubicin) which has been enriched with glycosphingolipid (for example, N-octanoyl-glucosylceramide, referred to herein as "$C_8$-GlcCer") greatly enhances drug transfer to tumor cells, in turn leading to an increased cytotoxicity. Furthermore, these glycosphingolipids have doxorubicin uptake-enhancing properties comparable to that of $C_6$-SM, but with a significantly lower toxicity. Incorporation of these glycosphingolipids into the liposome bilayer would effectively circumvent any solubility-related problems. Advantages of co-delivery of doxorubicin and the lipid analogue (within the same liposomal complex) include avoidance of lipid-solubility related toxicities and of differences in biodistribution. In addition, the steric barrier provided by PEG (for example, in PEG-liposome-encapsulated doxorubicin) would reduce any interaction of the glycosphingolipids with serum components. Such liposomes ensure co-delivery of the anthracycline (e.g., doxorubicin) and glycosphingolipid at the same site. Additionally, this effect was found to be fully reproducible in the presence of high serum concentrations, strongly supporting the feasibility of in vivo applications. These results were fully reproducible when N-octanoyl-glucosylceramide was post-inserted into Caelyx®, a commercial liposomal doxorubicin preparation. Taken together, these results demonstrate that glycosphingolipids-enrichment is a major improvement of a well established doxorubicin formulation.

The improved formulation offers many advantages. For example, the improved drug uptake permits the use of formulations with lower drug (e.g., amphiphilic drug) (e.g., anthracycline) (e.g., doxorubicin) content to achieve the same result, thereby reducing undesired side effects, e.g., myocardial toxicity.

Liotta et al., 1999 describes the use of certain sphingolipids, including certain glycosphingolipids (see, e.g., compounds listed from page 25 onwards therein) as active agents (e.g., drugs) in the treatment of abnormal cell proliferation. Although combination therapy is discussed (see, e.g., pages 72-73 therein), anthracyclines and doxorubicin are mentioned only as part of a long list of possible drugs. Although pharmaceutical compositions are discussed (see, e.g., starting on page 107 therein), liposomal suspensions and liposome formulations are mentioned (see, e.g., page 110 therein) only as part of a long list of possible formulations. In view of this document, and from among the myriad of other embodiments therein, both theoretical and exemplified, the skilled reader would not seriously contemplate pharmaceutical formulations comprising certain short-chain sphingolipids, as described herein, and drugs (e.g., anthracyclines), let alone corresponding liposomal formulations. Nowhere is there any teaching or suggestion of the use of short-chain sphingolipids as an adjunct to improved the efficacy of drugs (e.g., anthracyclines). Furthermore, the substantial improvement offered by such formulations (and demonstrated by the inventors) is both surprising and unexpected.

SUMMARY OF THE INVENTION

One aspect of the present invention pertains to pharmaceutical formulations which comprise (i) a drug (e.g., an amphiphilic drug) (e.g., an anthracycline) (e.g., doxorubicin) and (ii) a short-chain sphingolipid (e.g., a short-chain glycosphingolipid or a short-chain sphingomyelin) (e.g., N-octanoyl-glucosylceramide, referred to as $C_8$-GlcCer) (e.g., N-hexanoyl-sphingomyelin, referred to herein as $C_6$-SM), as described herein.

One aspect of the present invention pertains to pharmaceutical formulations which comprise (i) a drug and (ii) a short-chain sphingolipid, as described herein, for use in a method of treatment of the human or animal body by therapy.

One aspect of the present invention pertains use of (i) an antiproliferative drug and (ii) a short-chain sphingolipid, as described herein, in the manufacture of a medicament for the treatment of a proliferative condition in a human or animal patient.

One aspect of the present invention pertains to a method of treating a proliferative condition comprising administering to a patient in need of treatment an effective amount of a pharmaceutical formulation comprising (i) a drug and (ii) a short-chain sphingolipid, as described herein.

One aspect of the present invention pertains to a method of making a pharmaceutical formulation comprising the step of admixing (i) a drug and (ii) a short-chain sphingolipid, as described herein.

In one embodiment, the pharmaceutical formulation is a liposomal pharmaceutical formulation.

In one embodiment, the liposomes of the liposomal pharmaceutical formulation are prepared using a mixture of lipids comprising, at least, vesicle-forming lipids and said short-chain sphingolipid.

In one embodiment, the liposomes of the liposomal pharmaceutical formulation are prepared using a mixture of lipids comprising, at least, vesicle-forming lipids (e.g., phospholipids) (e.g., phosphatidylcholines) (e.g., fully hydrogenated soy phosphatidylcholine (HSPC)) (e.g., dipalmitoyl-phosphatidylcholine (DPPC)) and said short-chain sphingolipid.

In one embodiment, the mixture of lipids additional comprises cholesterol.

In one embodiment, the mixture of lipids additionally comprises a vesicle-forming lipid which is derivatized with a polymer chain (e.g., a phosphatidylethanolamine (PE) which is derivatized with polyethyleneglycol (PEG)) (e.g., N-(carbonyl-methoxypolyethylene glycol 2000)-1,2-distearoyl-sn-glycero-3-phosphoethanolamine sodium salt (MPEG2000-DSPE).

One aspect of the present invention pertains to a method of making a liposomal pharmaceutical formulation comprising the steps of:

(a) forming a lipid mixture comprising, at least, vesicle-forming lipids and a short-chain sphingolipid;

(b) forming liposomes from said lipid mixture; and (c) adding a drug to the liposomes formed in (b);

thereby forming liposome-entrapped drug.

One aspect of the present invention pertains to a method of making a liposomal pharmaceutical formulation comprising the steps of:

(a) forming a lipid mixture comprising, at least, vesicle-forming lipids and a short-chain sphingolipid;

(b) adding a drug to said lipid mixture;
(c) forming liposomes from the mixture formed in (b);
thereby forming liposome-entrapped drug.

One aspect of the present invention pertains to a method of increasing the bioavailability (and/or the cellular uptake) of a drug, which method includes the step of co-administering said drug with a short-chain sphingolipid, as described herein.

One aspect of the present invention pertains to certain novel short-chain sphingolipids, as described herein.

As will be appreciated by one of skill in the art, features and preferred embodiments of one aspect of the invention will also pertain to other aspects of the invention.

DETAILED DESCRIPTION

Pharmaceutical Formulations

Figure 1:
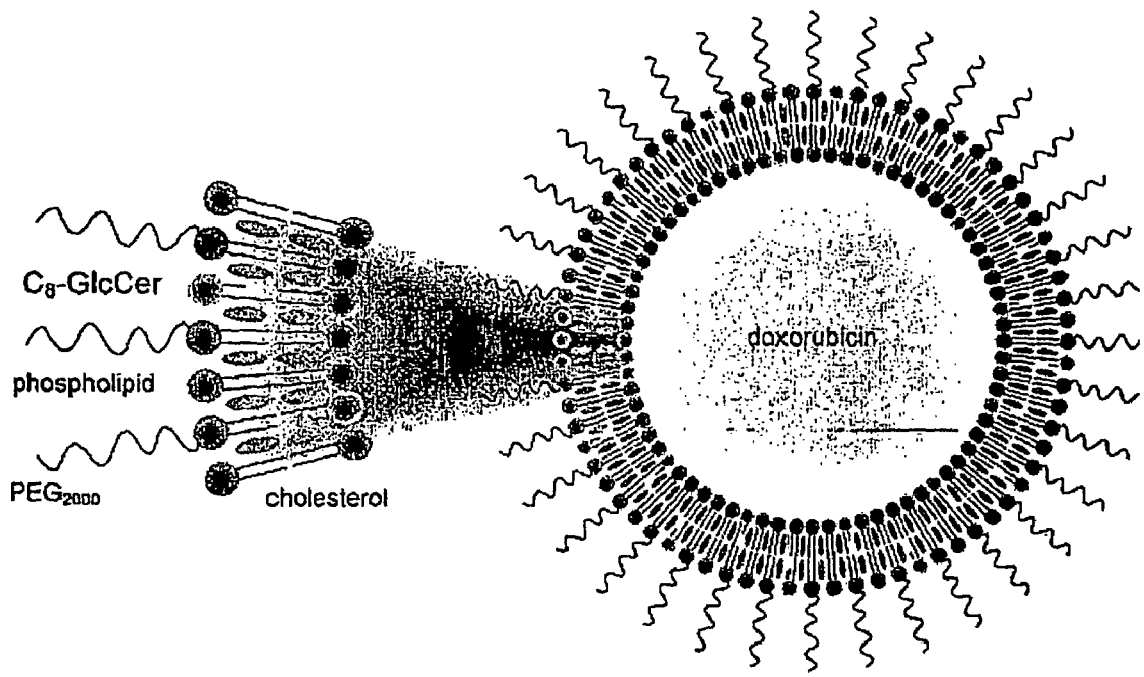
FIG. 1 is a schematic illustration of a liposome having a lipid bilayer formed from phospholipid, PEG2000 modified phospholipid, cholesterol, glycosphingolipid ($C_8$-GlcCer), and a liposome-entrapped drug (doxorubicin).

One aspect of the present invention pertains to pharmaceutical formulations (e.g., compositions, preparations, medicaments) which comprise (i) a drug (e.g., an amphiphilic drug) (e.g., an anthracycline) (e.g., doxorubicin) and (ii) a short-chain sphingolipid (e.g., a short-chain glycosphingolipid or a short-chain sphingomyelin) (e.g., N-octanoyl-glucosylceramide, referred to as $C_8$-GlcCer) (e.g., N-hexanoyl-sphingomyelin, referred to herein as $C_6$-SM), as described herein.

Such formulations may be conveniently referred to as "drug-sphingolipid" formulations (e.g., "anthracycline-sphingolipid" formulations) (e.g., "doxorubicin-sphingolipid" formulations).

Drugs—Amphiphilic Drugs

In one embodiment, the drug is an amphiphilic drug.

The terms "amphiphilic" and "amphipathic" are used herein interchangeably, and are used in the conventional sense to mean compounds (e.g., drugs) which are both (i) hydrophilic and (ii) hydrophobic (e.g., lipophilic).

The inventors have demonstrated that the delivery enhancement is not limited to a particular class of drugs (e.g., anthracyclines) but is in fact applicable to a range of drugs that are amphiphilic, for example, as characterised by their lipophilicity.

In one embodiment, the amphiphilic drug has a log(lipophilicity) value of 0.4 to 16.

In one embodiment, the lower limit is 0.5; the lower limit is 0.6; the lower limit is 0.8.

In one embodiment, the upper limit is 12; the upper limit is 10; the upper limit is 8.

For example, in one embodiment, the range is 0.8 to 8.

In this context, lipophilicity is defined as the 1-octanol/water partitioning ratio. The partitioning ratio is determined for 10-50 mM test compound (e.g., drug, probe) using a two phase system consisting of 1 mL 1-octanol and 1 mL water. After addition of the compound, tubes are vortexed and centrifuged (3000 rpm, 5 minutes, 20° C.). Aliquots of both the organic and the aqueous phases are taken for fluorimetric quantification. Native fluorescence intensities are measured, for example, by a Perkin-Elmer Victor Wallac II fluorescence microplate reader, using lex 485 nm and lem 535 nm filters. All values are corrected for background fluorescence. As a measure of lipophilicity, the 1-octanol/water partitioning ratio is calculated and expressed on a log scale (see, for example, Washington et al., 2001).

In one embodiment, the drug is an amphiphilic anti-proliferative drug.

In one embodiment, the drug is an amphiphilic anti-tumour drug.

In one embodiment, the drug is an amphiphilic anti-cancer drug.

In one embodiment, the drug is an amphiphilic anti-cancer drug from natural sources.

Drugs—Anthracyclines and Alkaloids

Many amphiphilic anti-cancer drugs from natural sources fall into two classes: Anthracyclines (such as doxorubicin, epirubicin, and daunorubicin), which are derived from microorganisms, which are believed to act by DNA intercalation); and Alkaloids (such as topotecan and camptothecin), which are derived from plants, and which are believed to act by inhibiting topoisomerase I. Other anti-cancer drugs with comparable amphiphilicity include, for example, teniposide, dactinomycin, raltitrexed, and irinotecan (CPT-11).

In one embodiment, the drug is an anthracycline (e.g., an amphiphilic anthracycline).

In one embodiment, the drug is an anti-proliferative anthracycline.

In one embodiment, the drug is an anti-tumour anthracycline.

In one embodiment, the drug is an anti-cancer anthracycline.

In one embodiment, the drug is selected from: doxorubicin, idarubicin, epirubicin, aclarubicin, mitrozantrone, and daunorubicin, and salts (e.g., acid addition salts) thereof.

In one embodiment, the drug is selected from doxorubicin and epirubicin, and salts (e.g., acid addition salts) thereof.

In one embodiment, the drug is doxorubicin or a salt (e.g., acid addition salt) thereof.

In one embodiment, the drug is doxorubicin or doxorubicin hydrochloride.

In one embodiment, included among anthracyclines are anthracycline-like drugs, such as dactinomycin.

In one embodiment, the drug is an alkaloid (e.g., an amphiphilic alkaloid).

In one embodiment, the drug is an anti-proliferative alkaloid.

In one embodiment, the drug is an anti-tumour alkaloid.

In one embodiment, the drug is an anti-cancer alkaloid.

In one embodiment, the drug is selected from: topotecan and camptothecin, and salts (e.g., acid addition salts) thereof.

Sphingolipids

The short-chain sphingolipids useful in the present invention are related to the following well known compounds, and may also be generally referred to as "sphingomyelin and cerebroside analogs."

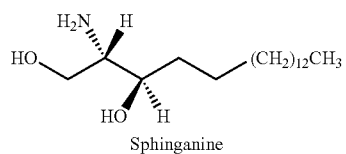

Sphinganine
(2S,3R or "D-erythro" configuration)
(also: dihydrosphingosine)

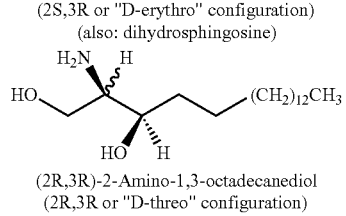

(2R,3R)-2-Amino-1,3-octadecanediol
(2R,3R or "D-threo" configuration)

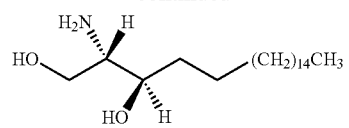

Icosasphinganine
(also: Eicosasphinganine)

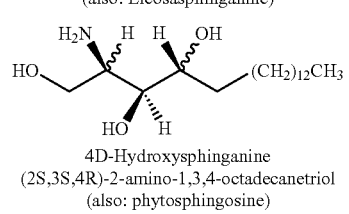

4D-Hydroxysphinganine
(2S,3S,4R)-2-amino-1,3,4-octadecanetriol
(also: phytosphingosine)

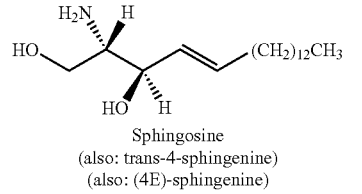

Sphingosine
(also: trans-4-sphingenine)
(also: (4E)-sphingenine)
(also: (2S,3R,4E)-2-amino-4-octadecene-1,3-diol)

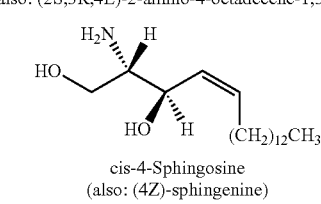

cis-4-Sphingosine
(also: (4Z)-sphingenine)

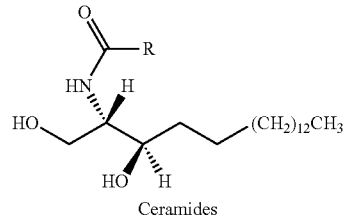

Ceramides

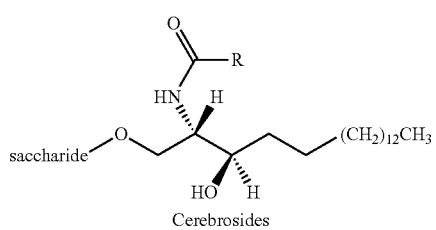

Cerebrosides

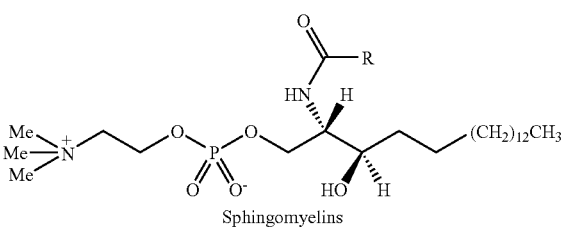

Sphingomyelins

Recommended naming practices for these and related lipids are discussed, for example, in the article by the IUPAC-IUB Commission on Biochemical Nomenclature: "The Nomenclature of Lipids (Recommendations 1976)," *Biochem. J.*, 1978, Vol. 171, pp. 21-33.

The short-chain sphingolipids useful in the present invention are selected from compounds of the following formula:

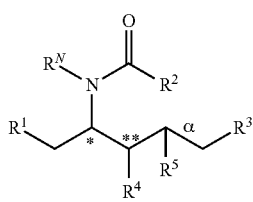

wherein:
R¹ is independently:
(for glycosphingolipids)
an O-linked saccharide group; or
an O-linked polyhydric alcohol group
or:
R¹ is independently:
(for sphingomyelins and other sphingoid-based phospholipids)
an O-linked (optionally N-($C_{1-4}$alkyl)-substituted amino)-$C_{1-6}$alkyl-phosphate group; or
an O-linked (polyhydric alcohol-substituted)-$C_{1-6}$alkyl-phosphate group;
$R^2$ is independently $C_{3-9}$alkyl,
and is independently unsubstituted or substituted;
$R^3$ is independently $C_{7-19}$alkyl,
and is independently unsubstituted or substituted;
$R^4$ is independently —H, —OH, or —O—$C_{1-4}$alkyl;
$R^N$ is independently —H or $C_{1-4}$alkyl;
the bond marked with an alpha (α) is independently a single bond or a double bond;
if the bond marked with an alpha (α) is a double bond, then $R^5$ is —H;
if the bond marked with an alpha (α) is a single bond, then $R^5$ is —H or —OH;
the carbon atom marked (*) is independently in an R-configuration or an S-configuration;
the carbon atom marked (**) is independently in an R-configuration or an S-configuration;
and pharmaceutically acceptable salts, solvates, esters, ethers, and chemically protected forms thereof.

The Substituent $R^2$: "Short Chain"

$R^2$ is independently $C_{3-9}$alkyl, and is independently unsubstituted or substituted.

The term "alkyl," as used herein, is intended to encompass aliphatic (i.e., linear or branched) saturated and partially unsaturated hydrocarbon groups, and so includes, for example, groups often referred to as "alkenyl" groups.

In one embodiment, $R^2$ is independently:
a $C_{5-9}$alkyl group; a $C_{7-9}$alkyl group; a $C_9$alkyl group;
a $C_{3-7}$alkyl group; a $C_{5-7}$alkyl group; a $C_7$alkyl group; a $C_5$alkyl group;
and is independently unsubstituted or substituted.

In one embodiment, $R^2$ is independently linear or branched.

In one embodiment, $R^2$ is independently linear.

In one embodiment, $R^2$ is independently branched.

In one embodiment, $R^2$ is independently saturated or partially unsaturated.

In one embodiment, $R^2$ is independently saturated.

In one embodiment, $R^2$ is independently partially unsaturated.

For example, in one embodiment, $R^2$ is independently linear or branched and saturated or partially unsaturated.

In one embodiment, $R^2$ independently has:
from 0 to 3 carbon-carbon double bonds;
from 1 to 3 carbon-carbon double bonds;
from 0 to 2 carbon-carbon double bonds;
from 1 to 2 carbon-carbon double bonds;
0 or 1 carbon-carbon double bond;
1 carbon-carbon double bond;
no carbon-carbon double bonds.

In one embodiment, the above double-bonds are cis-double bonds or trans-double bonds.

In one embodiment, the above double-bonds are cis-double bonds.

In one embodiment, the above double-bonds are trans-double bonds.

In one embodiment, $R^2$ is independently unsubstituted or substituted.

In one embodiment, $R^2$ is independently unsubstituted.

In one embodiment, $R^2$ is independently substituted.

In one embodiment, if $R^2$ is substituted, it is substituted with from 1 to 5 substituents.

In one embodiment, if $R^2$ is substituted, it is substituted with from 1 to 3 substituents.

In one embodiment, the substituents are selected from $C_{1-4}$alkyl, —OH, $C_{1-4}$alkoxy, —C(=O)OH, and —C(=O)O—$C_{1-4}$alkyl.

In one embodiment, the substituents are selected from -Me, -Et, —OH, —OMe, —OEt, —C(=O)OH, —C(=O)OMe, and —C(=O)OEt.

In one embodiment, the substituents are selected from -Me, —OH, —OMe, —C(=O)OH, and —C(=O)OMe.

Each compatible combination of the above features is also included as if it was explicitly recited. For example, in one embodiment, $R^2$ is a saturated linear $C_{5-9}$alkyl group which is unsubstituted, or substituted with from 1 to 3 substituents selected from -Me, —OH, —OMe, —C(=O)OH, and —C(=O)OMe.

In one embodiment, $R^2$ is independently —$(CH_2)_nCH_3$, wherein n is an integer from 2 to 8; from 4 to 8; from 6 to 8; 2 to 6; from 4 to 6; is 2; is 3; is 4; is 5; is 6; is 7; is 8.

In one embodiment, $R^2$ is independently —$(CH_2)_6CH_3$.

The Bond Marked Alpha (α)

The bond marked with an alpha (α) is independently a single bond or a double bond.

If the bond marked with an alpha (α) is a double bond, then $R^5$ is —H.

If the bond marked with an alpha (α) is a single bond, then $R^5$ is —H or —OH.

In one embodiment, the bond marked alpha is independently a double bond.

In one embodiment, the bond marked alpha is independently a cis-double bond.

In one embodiment, the bond marked alpha is independently a trans-double bond.

In one embodiment, the bond marked alpha is independently —CH=CH—.

In one embodiment, the bond marked alpha is independently cis —CH=CH—.

In one embodiment, the bond marked alpha is independently trans —CH=CH—.

In one embodiment, the bond marked alpha is independently an (Z)-double bond.

In one embodiment, the bond marked alpha is independently an (E)-double bond.

In one embodiment, the bond marked alpha is independently (Z)-CH=CH—.

In one embodiment, the bond marked alpha is independently (E)-CH=CH—.

In one embodiment, the bond marked alpha is independently a single bond; and $R^5$ is —H or —OH.

In one embodiment, the bond marked alpha is independently a single bond; and $R^5$ is —H.

In one embodiment, the bond marked alpha is independently a single bond; and $R^5$ is —OH.

In one embodiment, the bond marked alpha is independently —CH$_2$—CH$_2$—.

In one embodiment, the bond marked alpha is independently —CHOH—CH$_2$—.

If $R^5$ is —OH, then the carbon atom to which $R^5$ is attached is independently in an R-configuration or an S-configuration.

In one embodiment, if $R^5$ is —OH, then the carbon atom to which $R^6$ is attached is independently in an R-configuration.

In one embodiment, if $R^5$ is —OH, then the carbon atom to which $R^5$ is attached is independently in an S-configuration.

The Substituent $R^3$ $R^3$ is independently $C_{7-19}$alkyl, and is independently unsubstituted or substituted.

In one embodiment, $R^3$ is independently:
a $C_{7-19}$alkyl group; a $C_{9-19}$alkyl group; a $C_{11-19}$alkyl group; a $C_{13-19}$alkyl group;
a $C_{7-17}$alkyl group; a $C_{9-17}$alkyl group; a $C_{11-17}$alkyl group; a $C_{13-17}$alkyl group;
a $C_{7-15}$alkyl group; a $C_{9-15}$alkyl group; a $C_{11-15}$alkyl group; a $C_{13-15}$alkyl group;
a $C_{7-13}$alkyl group; a $C_{9-13}$alkyl group; a $C_{11-13}$alkyl group; a $C_{13}$alkyl group;
and is independently unsubstituted or substituted.

In one embodiment, $R^3$ is independently linear or branched.

In one embodiment, $R^3$ is independently linear.

In one embodiment, $R^3$ is independently branched.

In one embodiment, $R^3$ is independently saturated or partially unsaturated.

In one embodiment, $R^3$ is independently saturated.

In one embodiment, $R^3$ is independently partially unsaturated.

In one embodiment, $R^3$ independently has:
from 0 to 3 carbon-carbon double bonds;
from 1 to 3 carbon-carbon double bonds;
from 0 to 2 carbon-carbon double bonds;
from 1 to 2 carbon-carbon double bonds;
0 or 1 carbon-carbon double bond;
1 carbon-carbon double bond;
no carbon-carbon double bonds.

In one embodiment, the above double-bonds are trans-double bonds.

In one embodiment, $R^3$ is independently unsubstituted or substituted.

In one embodiment, $R^3$ is independently unsubstituted.

In one embodiment, $R^3$ is independently substituted.

In one embodiment, if $R^3$ is substituted, it is substituted with from 1 to 5 substituents.

In one embodiment, if $R^3$ is substituted, it is substituted with from 1 to 3 substituents.

In one embodiment, the substituents are selected from $C_{1-4}$alkyl, —OH, $C_{1-4}$alkoxy.

In one embodiment, the substituents are selected from -Me, -Et, —OH, —OMe, —OEt.

In one embodiment, the substituents are selected from -Me, —OH, —OMe.

Each compatible combination of the above features is also included as if it was explicitly recited. For example, in one embodiment, $R^3$ is a saturated linear $C_{11-15}$alkyl group which is unsubstituted, or substituted with from 1 to 3 substituents selected from -Me, —OH, and —OMe.

In one embodiment, $R^3$ is independently —(CH$_2$)$_n$CH$_3$, wherein n is an integer:
from 6 to 18; from 8 to 18; from 10 to 18; from 12 to 18;
from 6 to 16; from 8 to 16; from 10 to 16; from 12 to 16;
from 6 to 14; from 8 to 14; from 10 to 14; from 12 to 14;
from 6 to 12; from 8 to 12; from 10 to 12.

In one embodiment, $R^3$ is independently —(CH$_2$)$_{12}$CH$_3$.

Certain Combinations of α, $R^5$, and $R^3$

In one embodiment, the moiety:

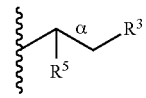

is selected from the following:
—(CH$_2$)$_8$—CH$_3$ (from caproic acid) ("C10");
—(CH$_2$)$_{10}$—CH$_3$ (from lauric acid) ("C12");
—(CH$_2$)$_{12}$—CH$_3$ (from myristic acid) ("C14");
—(CH$_2$)$_{14}$—CH$_3$ (from palmitic acid) ("C16");
—(CH$_2$)$_7$—CH=CH—(CH$_2$)$_5$—CH$_3$ (from palmitoleic acid) ("C16");
—(CH$_2$)$_{16}$—CH$_3$ (from stearic acid) ("C18");
—(CH$_2$)$_7$—CH=CH—(CH$_2$)$_7$—CH$_3$ (from oleic acid) ("C18");
—(CH$_2$)$_9$—CH=CH—(CH$_2$)$_5$—CH$_3$ (from vaccenic acid) ("C18");
—(CH$_2$)$_7$—[CH=CH—CH$_2$]$_2$—(CH$_2$)$_3$—CH$_3$ (from linoleic acid) ("C18");
—(CH$_2$)$_7$—[CH=CH—CH$_2$]$_3$—CH$_3$ (from (9,12,15-linoleic acid) ("C18");
—(CH$_2$)$_4$—[CH=CH—CH$_2$]$_3$—(CH$_2$)$_3$—CH$_3$ (from (6,9,12-linoleic acid) ("C18");
—(CH$_2$)$_7$—[CH=CH]$_3$—(CH$_2$)$_3$—CH$_3$ (from eleostearic acid) ("C18");
—(CH$_2$)$_{18}$—CH$_3$ (from arachidic acid) ("C20");
—(CH$_2$)$_6$—[CH=CH—CH$_2$]$_2$—(CH$_2$)$_6$—CH$_3$ ("C20");
—(CH$_2$)$_3$—[CH=CH—CH$_2$]$_3$—(CH$_2$)$_6$—CH$_3$ ("C20");
—(CH$_2$)$_3$—[CH=CH—CH$_2$]$_4$—(CH$_2$)$_3$—CH$_3$ ("C20");
—(CH$_2$)$_{20}$—CH$_3$ (from behenoic acid) ("C22");
analogs wherein the left-most —(CH$_2$)$_2$— is replaced with —CH=CH—; and
analogs wherein the left-most —(CH$_2$)— is replaced with —CH(OH)—.

The Substituent $R^4$ $R^4$ is independently —H, —OH, or —O—$C_{1-4}$alkyl (e.g., saturated aliphatic —O—$C_{1-4}$alkyl).

In one embodiment, $R^4$ is independently —H, —OH, —OMe, —OEt, —O(iPr), —O(nPr), —O(nBu), —O(iBu), —O(sBu), or —O(tBu).

In one embodiment, $R^4$ is independently —H, —OH, —OMe, or —OEt.

In one embodiment, $R^4$ is independently —H, —OH, or —OMe.

In one embodiment, $R^4$ is independently —H or —OH.

In one embodiment, $R^4$ is independently —OH or —O—$C_{1-4}$alkyl.

In one embodiment, $R^4$ is independently —OH, —OMe, —OEt, —O(iPr), —O(nPr), —O(nBu), —O(iBu), —O(sBu), or —O(tBu).

In one embodiment, $R^4$ is independently —OH, —OMe, or —OEt.

In one embodiment, $R^4$ is independently —OH or —OMe.

In one embodiment, $R^4$ is independently —H.

In one embodiment, $R^4$ is independently —OH.

In one embodiment, $R^4$ is independently —O—$C_{1-4}$alkyl.

In one embodiment, $R^4$ is independently —OMe or —OEt.
In one embodiment, $R^4$ is independently —OH or —OMe.
The Substituent $R^N$ $R^N$ is independently —H or $C_{1-4}$alkyl.

In one embodiment, $R^N$ is independently —H or linear or branched saturated $C_{1-4}$alkyl.

In one embodiment, $R^N$ is independently —H, -Me, -Et, -iPr, -nPr, -nBu, -iBu, -sBu, or -tBu.

In one embodiment, $R^N$ is independently —H, -Me, or -Et.

In one embodiment, $R^N$ is independently —H or -Me.

In one embodiment, $R^N$ is independently —H.

In one embodiment, $R^N$ is independently -Me, -Et, -iPr, -nPr, -nBu, -iBu, -sBu, or -tBu.

In one embodiment, $R^N$ is independently -Me or -Et.

The Carbon Atoms Marked (*) and (**)

The carbon atom marked (*) is independently in an R-configuration or an S-configuration.

The carbon atom marked (**) is independently in an R-configuration or an S-configuration.

In one embodiment, the carbon atom marked (*) is in an R-configuration and the carbon atom marked (**) is in an R-configuration.

In one embodiment, the carbon atom marked (*) is in an R-configuration and the carbon atom marked (**) is in an S-configuration.

In one embodiment, the carbon atom marked (*) is in an S-configuration and the carbon atom marked (**) is in an R-configuration.

In one embodiment, the carbon atom marked (*) is in an S-configuration and the carbon atom marked (**) is in an S-configuration.

In one embodiment, the carbon atom marked (*) and the carbon atom marked (**) are in a D-erythro configuration.

In one embodiment, the carbon atom marked (*) and the carbon atom marked (**) are in an L-erythro configuration.

In one embodiment, the carbon atom marked (*) and the carbon atom marked (**) are in a D-threo configuration.

In one embodiment, the carbon atom marked (*) and the carbon atom marked (**) are in an L-threo configuration.

In one embodiment, the carbon atoms marked (*) and (**) have a configuration as shown in the following formula:

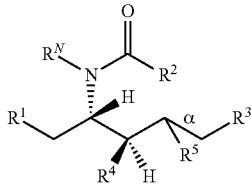

In one embodiment, the carbon atoms marked (*) and (**) have the same configuration as in naturally occurring sphingosine (also known as (2S,3R,4E)-2-amino-4-octadecene-1, 3-diol; (E)-D-erythro-4-octaadecene-1,3-diol; 1,3-dihydroxy-2-amino-4-octadecene; 4-sphingenine):

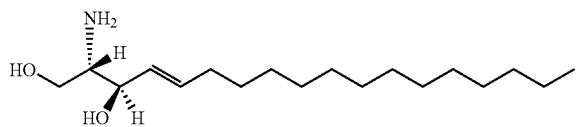

The Substituent $R^1$: Glycosphingolipids

The term "glycosphingolipids," as used in this context, pertains to both glycosphingolipids (which bear an O-linked saccharide group) as well as analogs which bear an O-linked polyhydric alcohol group, as described below.

In one embodiment (for short-chain glycosphingolipids), $R^1$ is independently:
an O-linked saccharide group; or
an O-linked polyhydric alcohol group.

The term "O-linked", as used in this context, pertains to a saccharide group or polyhydric alcohol group which is attached to the sphingolipid via an ether bond (—O—) that is formed from a hydroxy group (—OH) of the parent saccharide (e.g., as in a glycosyl group) or parent polyhydric alcohol.

Saccharide Groups

An example of a parent saccharide (β-D-glucopyranose) and an O-linked saccharide group (D-glucopyranosyl-β1-) are shown below.

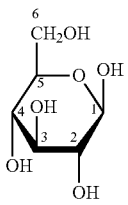
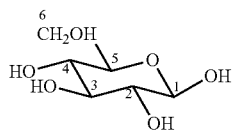
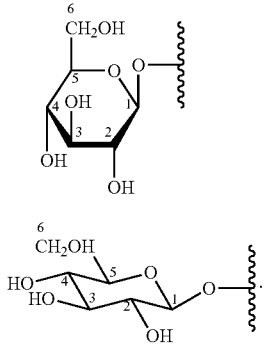

β-D-glucopyranose      D-glucopyranosyl-β1–

The corresponding example of a glycosphingolipid is shown below:

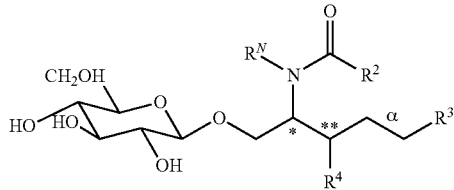

Another example of a parent saccharide (β-D-galactopyranose) and an O-linked saccharide group (D-galactopyranosyl-β1-) are shown below.

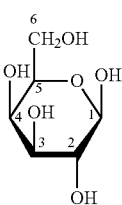
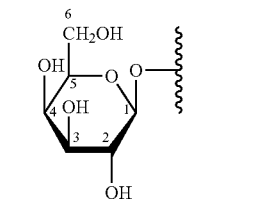

β-D-galactopyranose      D-galactopyranosyl-β1–

The corresponding example of a glycosphingolipid is shown below:

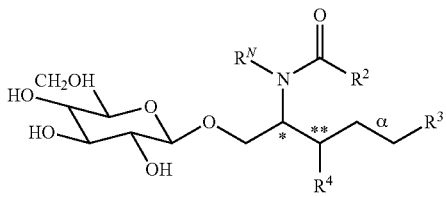

Another example of a parent saccharide (lactose; 4-O-β-D-galactopyranosyl-D-glucose) and an O-linked saccharide group (lactosyl-β1-) are shown below.

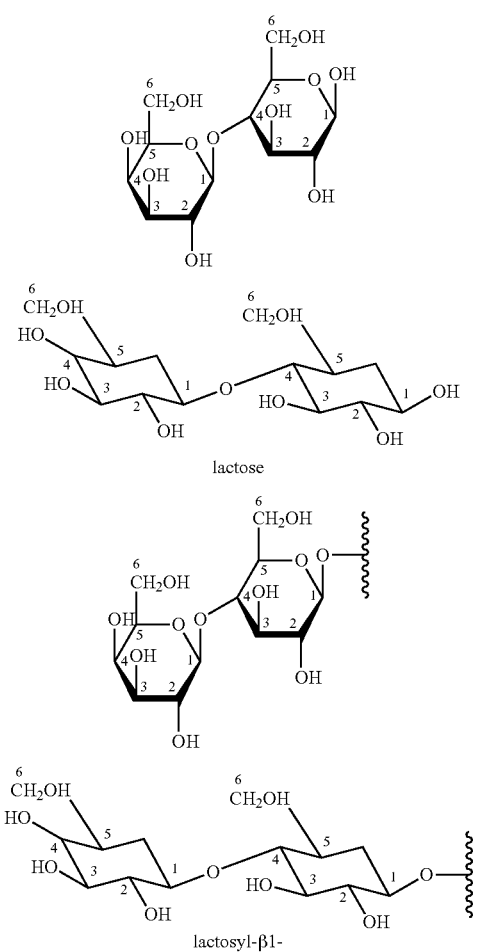

The corresponding example of a glycosphingolipid is shown below:

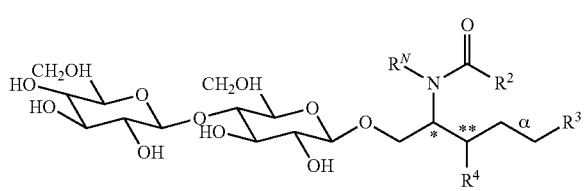

Saccharides are carbohydrates which can be considered to be hydroxylated aldehydes and ketones. If two or more monosaccharides are linked, for example, via an acetal linkage (e.g., a 1,4-acetal linkage), the compound is conventionally referred to as a disaccharide (also referred to as a -biose) (e.g., sucrose, maltose, lactose, cellobiose, galabiose), trisaccharide (also referred to as a -triaose) (e.g., globotriaose, isoglobotriaose, mucotriaose, lactotriaose, neolactotriaose, gangliotriaose, galatriaose, mollutriaose, antrotriaose), etc., and in general, as polysaccharides (also known as glycans, e.g., cellulose, starch, glycogen, amylose, amylopectin).

Monosaccharides are conventionally named according to the overall number of carbon atoms, for example, tri-($C_3$), tetr-($C_4$), pent-($C_5$), and hex-($C_6$). Monosaccharides may be in, for example, aldose, ketose, aldoketose, and dialdose form. Aldoses are conventionally named as -ose, for example, triose ($C_3$), tetrose ($C_4$), pentose ($C_5$), hexose ($C_6$), and heptose ($C_7$). Ketoses are conventionally named as -ulose, for example, tetrulose ($C_4$), pentulose ($C_5$), hexulose ($C_6$), and heptulose ($C_7$). Aldoketoses are conventionally named as -osulose. Dialdoses are conventionally named as -odialdose.

Monosaccharides may have one or more chiral centres, and thus may have different stereoisomeric forms (e.g., R-, S-, D-, L-, α-, β-, (+), (−), and combinations thereof, e.g., α-D-, β-D-, α-L-, β-L-). Isomers which are superimposable mirror images are conventionally referred to as enantiomers. Isomers which differ from each other by the configuration at two or more chiral centres are conventionally referred to as diastereiomers. Isomers which differ from each other by the configuration at only one chiral centre are conventionally referred to as epimers (e.g., D-ribose and D-xylose).

The configuration at each chiral centre is conventionally denoted R or S. The prefixes D- or L- are conventionally used to indicate monosaccharides with a configuration that is related to D- and L-glyceraldehyde, respectively. The prefixes (+)- and (−)- are conventionally used to indicated monosaccharides which are dextrorotatory (rotate the plane of polarised light to the right, in a clockwise direction) or levorotatory (to the left, in a counter-clockwise direction), respectively.

The prefixes erythro- and threo-denote certain tetrose ($C_4$) diastereomers. The prefixes arabino-, lyxo-, ribo-, and xylo-denote certain pentose ($C_5$) diasteriomers. The prefixes allo-, altro-, gluco-, manno-, gulo-, ido-, galacto-, and talo-denote certain hexose ($C_6$) diasteriomers.

In cyclic form (hemiacetal or hemiketal form), monosaccharides are conventionally named according to the number of ring atoms. For example, a furanose has a 5-membered ring; a pyranose has a 6-membered ring; a septanose has a 7-membered ring. The prefixes α- and β- are conventionally used to indicate the two anomers which arise from the new chiral centre which is formed upon cyclisation.

Examples of monosaccharides include, but are not limited to, the following, which may be in a α-D, β-D, α-L, or β-L form:
erythrose and threose;
arabinose, lyxose, ribose, and xylose;
allose, altrose, glucose, mannose, gulose, idose, galactose, and talose;
arabinofuranose, lyxofuranose, ribofuranose, and xylofuranose;
allofuranose, altrofuranose, glucofuranose, mannofuranose, gulofuranose, idofuranose, galactofuranose, talofuranose;
allopyranose, altropyranose, glucopyranose, mannopyranose, gulopyranose, idopyranose, galactopyranose, and talopyranose.

Many saccharides are known by their trivial names, for example, D-threose (D-threo-tetrose), D-ribose (D-ribo-pentose), D-galactose (D-galacto-hexose), D-fructose (D-arabino-2-hexulose), L-sorbose (L-xylo-2-hexulose), D-ribulose (D-erythro-2-pentulose), D-sedoheptulose (D-altro-2-heptulose).

Many saccharides derivatives are well known, for example, deoxy-saccharides (e.g., 6-deoxy-L-galactose, also known as L-fucose; 6-deoxy-L-mannose, also known as L-rhamnose; 2-deoxy-D-erythro-pentose, also known as deoxyribose or 2-deoxy-D-ribose); glycosides (e.g., methyl α-D-glucopyranoside); amino-deoxy-saccharides, also known as glucosamines (e.g., D-glucosamine, D-galactosamine); alditols (e.g., D-glutitol, also known as D-sorbitol; D-mannitol; meso-galactitol); aldonic acids, also known as glyconic acids (e.g., D-gluconic acid); uronic acids, also known as glycouronic acids (e.g., D-galactouronic acid); and aldaric acids, also known as glycaric acids (e.g., L(+)-tartaric acid).

In one embodiment, $R^1$ is independently an O-linked mono-, di-, or tri-saccharide group.

In one embodiment, $R^1$ is independently an O-linked mono- or di-saccharide group.

In one embodiment, $R^1$ is independently an O-linked mono-saccharide group.

In one embodiment, $R^1$ is independently an O-linked di-saccharide group.

In one embodiment, $R^1$ is independently an O-linked tri-saccharide group.

In one embodiment, $R^1$ is independently an O-linked mono-, di-, or tri-saccharide group (as defined above) formed from pentose and/or hexose groups.

In one embodiment, $R^1$ is independently an O-linked mono-, di-, or tri-saccharide group derived from:
arabinose, lyxose, ribose, or xylose;
allose, altrose, glucose, mannose, gulose, idose, galactose, or talose;
sucrose, maltose, lactose, cellobiose, or galabiose;
globotriaose, isoglobotriaose, mucotriaose, lactotriaose, neolactotriaose gangliotriaose, galatriaose, mollutriaose, or antrotriaose;
or a derivative thereof.

In one embodiment, $R^1$ is independently an O-linked mono-, di-, or tri-saccharide group (as defined above) formed from furanose and/or pyranose monosaccharide groups, for example, as described above.

In one embodiment, $R^1$ is independently an O-linked di-saccharide group (as defined above) formed from furanose and/or pyranose monosaccharide groups, for example, as described above.

In one embodiment, $R^1$ is independently an O-linked tri-saccharide group (as defined above) formed from furanose and/or pyranose monosaccharide groups, for example, as described above.

In one embodiment, $R^1$ is independently an O-linked mono-, di-, or tri-saccharide group derived from:
arabinofuranose, lyxofuranose, ribofuranose, or xylofuranose;
allofuranose, altrofuranose, glucofuranose, mannofuranose, gulofuranose, idofuranose, galactofuranose, or talofuranose;
allopyranose, altropyranose, glucopyranose, mannopyranose, gulopyranose, idopyranose, galactopyranose, or talopyranose;
sucrose, maltose, lactose, cellobiose, or galabiose;
globotriaose, isoglobotriaose, mucotriaose, lactotriaose, neolactotriaose gangliotriaose, galatriaose, mollutriaose, or antrotriaose;
or a derivative thereof.

In one embodiment, $R^1$ is independently an O-linked monosaccharide group derived from: glucofuranose, galactofuranose, glucopyranose, or galactopyranose; or a derivative thereof.

In one embodiment, $R^1$ is independently an O-linked disaccharide group derived from: sucrose, maltose, lactose, cellobiose, or galabiose; or a derivative thereof.

In one embodiment, $R^1$ is independently an O-linked trisaccharide group derived from: globotriaose, isoglobotriaose, mucotriaose, lactotriaose, neolactotriaose gangliotriaose, galatriaose, mollutriaose, or antrotriaose; or a derivative thereof.

In one embodiment, $R^1$ is independently an O-linked monosaccharide group derived from: glucopyranose or galactopyranose; or a derivative thereof.

In one embodiment, $R^1$ is independently an O-linked monosaccharide group derived from: glucopyranose; or a derivative thereof.

In one embodiment, $R^1$ is independently an O-linked monosaccharide group derived from a furanose or pyranose (as defined above), and is α-L, α-D, β-L, or β-D.

In one embodiment, $R^1$ is independently an O-linked monosaccharide group derived from a furanose or pyranose (as defined above), and is β-D.

In one embodiment, $R^1$ is independently an O-linked monosaccharide group derived from: β-D-glucopyranose or β-D-galactopyranose; or a derivative thereof.

In one embodiment, $R^1$ is independently a 1-O-linked saccharide group, and optionally additionally as defined above.

In one embodiment, $R^1$ is independently a β1-O-linked saccharide group, and optionally additionally as defined above.

In one embodiment, $R^1$ is independently D-glucopyranosyl-β1- or D-galactopyranosyl-β1-; or a derivative thereof.

In one embodiment, $R^1$ is independently an O-linked monosaccharide group derived from a ganglioside (e.g., a monosialoganglioside).

In one embodiment, $R^1$ is independently an O-linked mono-, di-, or trisaccharide group derived from:
I$^3$NeuAc-Gal
II$^3$NeuAc-Lac ("$G_{M3}$")
II$^3$NeuGc-Lac
II$^3$(NeuAc)$_2$-Lac ("$G_{D3}$")
II$^3$NeuAc/NeuGc-Lac
II$^3$NeuGc-Lac
II$^3$NeuAc-GgOse$_3$ ("$G_{M2}$")
II$^3$NeuAc-GgOse$_4$ ("$G_{M1}$")
IV$^3$NeuAc-nLcOse$_3$ ("$G_{M1\text{-}GlCNAc}$")
IV$^6$NeuAc-nLcOse$_3$
IV$^2$Fuc,II$^3$NeuAc-GgOse$_4$
IV$^3$NeuAc-nLcOse$_3$
II$^3$(NeuAc)$_2$-GgOse$_4$ ("$G_{D1b}$")
IV$^3$NeuAc,II$^3$NeuAc-GgOse$_4$ ("$G_{D1a}$")
II$^3$(NeuAc)$_3$-GgOse$_4$
IV$^3$NeuAc,II$^3$(NeuAc)$_2$-GgOse$_4$
IV$^3$NeuAc,II$^3$(NeuAc)$_3$-GgOse$_4$
IV$^3$(NeuAc)$_2$,II$^3$(NeuAc)$_3$-GgOse$_4$
IV$^3$NeuAc,II$^3$NeuAc-GgOse$_5$ Saccharide Derivatives In one embodiment, the derivative thereof is a deoxy, di-deoxy, di-deoxy-di-dehydro, methoxy (—OMe), acetoxy (—OC(=O)Me), carboxylic acid (—C(=O)OH), sulfuric acid (—OSO$_3$H), amino-deoxy (e.g., —NH$_2$), N-acetyl-amino-deoxy (e.g., —NHC(=O)Me), or N-sulfo-amino-deoxy (e.g., —NHS(O)$_2$OH) derivative thereof.

Examples of such derivatives are shown below.

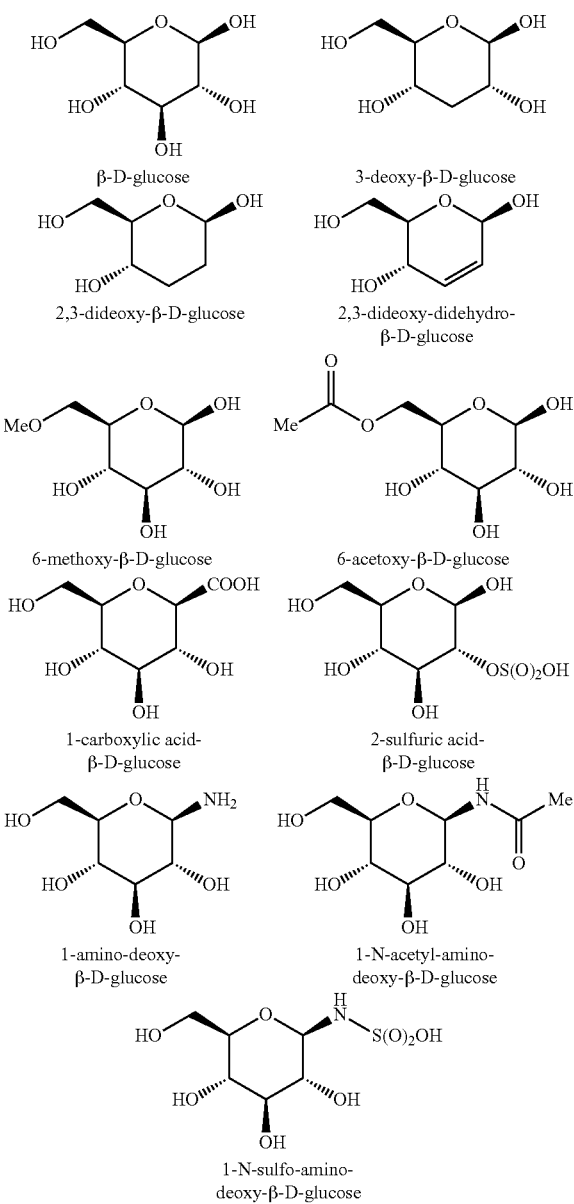

Polyhydric Alcohols

Polyhydric alcohols are alcohols that have more than one hydroxyl (—OH) group, and are often referred to as "polyols."

Examples of polyhydric alcohols include: ethanediol (glycol), propanediol, butanediol, glycerol, and erythritol.

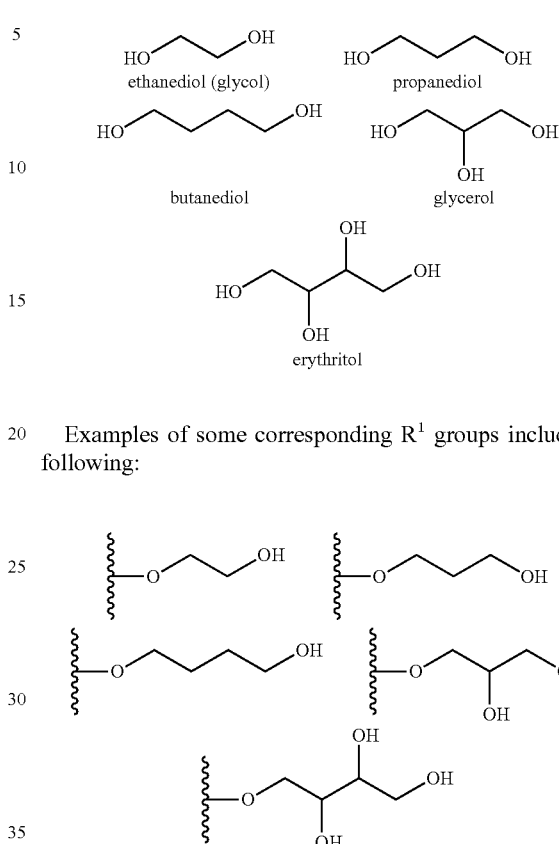

Examples of some corresponding $R^1$ groups include the following:

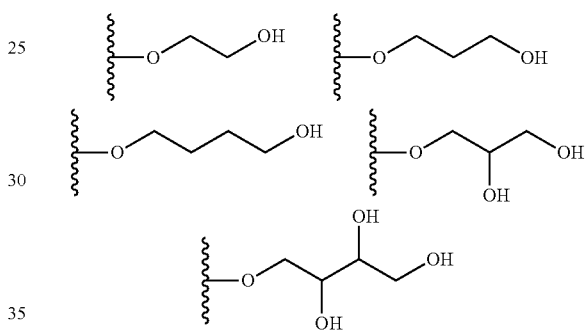

Some Preferred Glycosphingolipids

In one embodiment, the compound has the following formula:

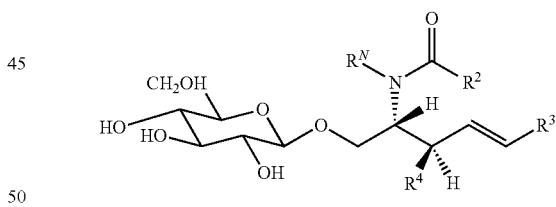

In one embodiment, the compound has the following formula ($C_8$-GlcCer):

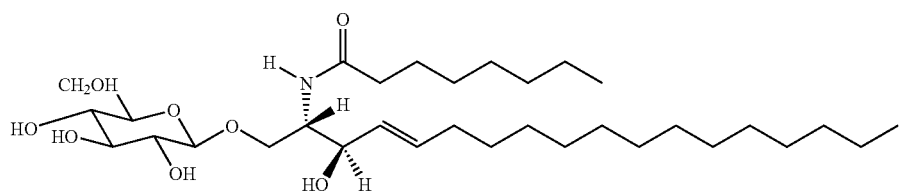

In one embodiment, the compound has the following formula:

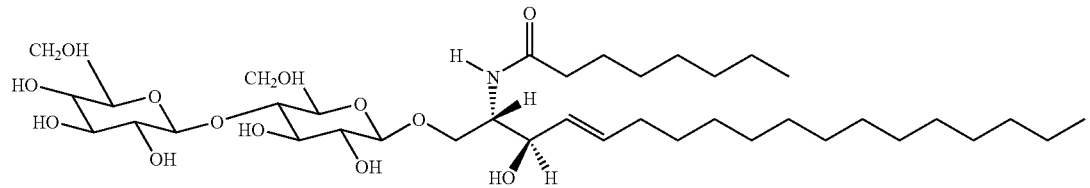

The Substituent R¹: Sphingomyelins

The term "sphingomyelins," as used in this context, pertains to both sphingomyelins (which bear a phosphocholine group) as well as sphingomyelin analogs which bear an analog of a phosphocholine group, for example, as described below, or polyhydric alcohol analogs, which bear a polyhydric alcohol groups, as described below. These compounds may be conveniently described as "sphingomyelins and other sphingoid-based phos,pholipids."

In one embodiment, R¹ is independently:
an O-linked (optionally N—($C_{1-4}$alkyl)-substituted amino)-$C_{1-6}$alkyl-phosphate group (e.g., a phosphatidyl choline-like group); or:
an O-linked (polyhydric alcohol-substituted)-$C_{1-6}$alkyl-phosphate group.

The term "O-linked", as used in this context, pertains to an amino-$C_{1-6}$alkyl group or a (polyhydric alcohol-substituted)-$C_{1-6}$alkyl group which is attached to the sphingolipid via a phosphate bridge of the following formula:

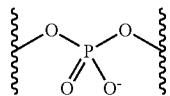

In one embodiment, the $C_{1-6}$alkyl group is a linear or branched saturated $C_{1-6}$alkyl group.

In one embodiment, the $C_{1-6}$alkyl group is a linear saturated $C_{1-6}$alkyl group.

In one embodiment, the $C_{1-6}$alkyl group is —$(CH_2)_q$—$CH_2$— wherein q is independently an integer from 0 to 5.

In one embodiment, the $C_{1-6}$alkyl group is —$CH_2$—$CH_2$—.

In one embodiment, R¹ is independently an O-linked (optionally N—($C_{1-4}$alkyl)-substituted amino)-$C_{1-6}$alkyl-phosphate group (e.g., a phosphatidyl choline-like group).

The term "optionally N—($C_{1-4}$alkyl)-substituted amino," as used in this context, pertains to the following groups: unsubstituted amino (e.g., —$NH_2$), mono-substituted amino (i.e., —$NHR^a$), di-substituted amino (i.e., —$NR^a_2$), and tri-substituted amino (i.e., —$NR^a_3{}^+$), wherein each $R^a$ is independently saturated linear or branched $C_{1-4}$alkyl.

In one embodiment, R¹ is independently an O-linked (polyhydric alcohol-substituted)-$C_{1-6}$alkyl-phosphate group.

The term "(polyhydric alcohol-substituted)-$C_{1-6}$alkyl," as used in this context, pertains to a $C_{1-6}$alkyl which bears a polyhydric alcohol group, linked via an oxygen atom (i.e., the oxygen atom of one of its hydroxyl groups).

In one embodiment, R¹ is independently a group of the following formula:

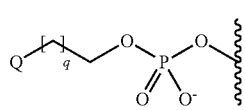

wherein:
q is independently an integer from 0 to 5;

Q is independently: —$NH_2$, —$NHR^a$, —$NR^a_2$, or —$NR^a_3{}^+$; or:

Q is independently a polyhydric alcohol group, linked via an oxygen atom; and
each $R^a$ is independently linear or branched saturated $C_{1-4}$alkyl.

In one embodiment, Q is independently: —$NH_2$, —$NHR^a$, —$NR^a_2$, or —$NR^a_3{}^+$.

In one embodiment, R¹ is independently an O-linked N,N,N-tri($C_{1-4}$alkyl)-substituted amino-$C_{1-6}$alkyl-phosphate group of the following formula:

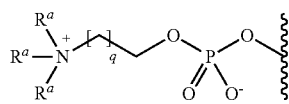

wherein:
q is independently an integer from 0 to 5; and
each $R^a$ is independently a linear or branched saturated $C_{1-4}$alkyl group.

In one embodiment, Q is independently a polyhydric alcohol group, linked via an oxygen atom, as in, for example, the following groups, where q is independently an integer from 0 to 5:

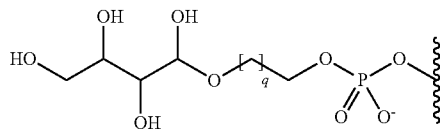

In one emobodiment, q is independently: an integer from 0 to 4; from 0 to 3; from 0 to 2; from 0 to 1; from 1 to 5; from 1 to 4; from 1 to 3; from 1 to 2; 5; 4; 3; 2; 1; or 0.

In one embodiment, each Ra is independently -Me, -Et, -iPr, -nPr, -nBu, -sBu, -iBu, or -tBu.

In one embodiment, each $R^a$ is independently -Me or -Et.

In one embodiment, each $R^a$ is independently -Me.

In one embodiment, R¹ is independently:

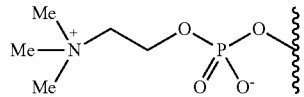

In one embodiment, the sphingomyelin is independently ("$C_6$-SM"):

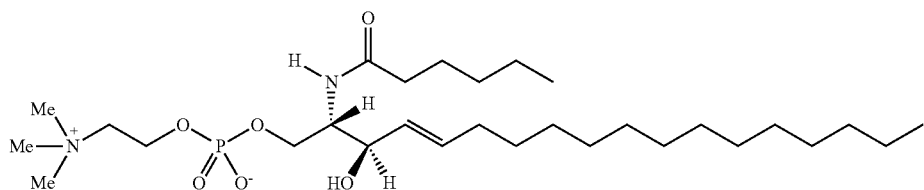

In one embodiment, the sphingomyelin is independently ("3-O-methyl-$C_8$-SM"):

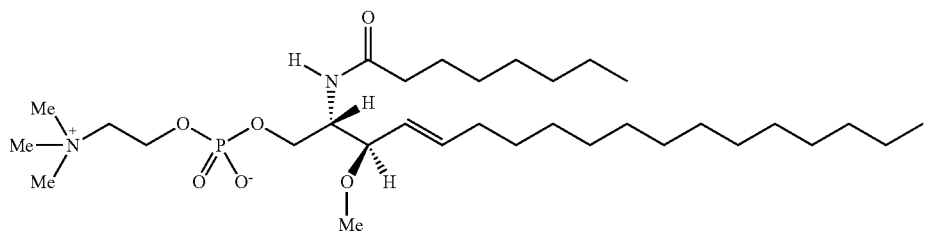

Pharmaceutical Formulations—Additional Ingredients

One aspect of the present invention pertains to pharmaceutical formulations (e.g., compositions, preparations, medicaments) which comprise (i) a drug (e.g., an anthracycline) (e.g., doxorubicin) and (ii) a short-chain sphingolipid (e.g., a short-chain glycosphingolipid or a short-chain sphingomyelin) (e.g., N-octanoyl-glucosylceramide, referred to as $C_8$-GlcCer) (e.g., N-hexanoyl-sphingomyelin, referred to herein as $C_6$-SM), as described herein.

In one embodiment, the formulations additionally comprise one or more other pharmaceutically acceptable ingredients well known to those skilled in the art, including, but not limited to, pharmaceutically acceptable carriers, diluents, excipients, adjuvants, fillers, buffers, preservatives, anti-oxidants, lubricants, stabilisers, solubilisers, and surfactants.

Suitable carriers, diluents, excipients, etc. can be found in standard pharmaceutical texts. See, for example, *Handbook of Pharmaceutical Additives*, 2nd Edition (eds. M. Ash and I. Ash), 2001 (Synapse Information Resources, Inc., Endicott, N.Y., USA), *Reminqton's Pharmaceutical Sciences*, 20th edition, pub. Lippincott, Williams & Wilkins, 2000; and *Handbook of Pharmaceutical Excipients*, 2nd edition, 1994.

In one embodiment, the formulations further comprises other active agents, for example, other therapeutic or prophylactic agents.

The term "pharmaceutically acceptable" as used herein pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

Pharmaceutical Formulations—Methods of Preparation

One aspect of the present invention pertains to a method of making a pharmaceutical formulation comprising the step of admixing (i) a drug (e.g., an amphiphilic drug) (e.g., an anthracycline) (e.g., doxorubicin) and (ii) a short-chain sphingolipid (e.g., a short-chain glycosphingolipid or a short-chain sphingomyelin) (e.g., N-octanoyl-glucosylceramide, referred to as $C_8$-GlcCer) (e.g., N-hexanoyl-sphingomyelin, referred to herein as $C_6$-SM), as described herein. If formulated as discrete units (e.g., ampoules, etc.), each unit contains a predetermined amount (dosage) of the drug (e.g., amphiphilic drug) (e.g., anthracycline) (e.g., doxorubicin) and short-chain sphingolipid.

The formulations may be prepared by any methods well known in the art of pharmacy. Such methods include the step of bringing into association the active compound with a carrier which constitutes one or more accessory ingredients. In general, the formulations are prepared by uniformly and intimately bringing into association the drug and short-chain sphingolipid, and optionally other pharmaceutically acceptable carriers, diluents, excipients, etc., and then shaping the product, if necessary.

The formulation may be prepared to provide for rapid or slow release; immediate, delayed, timed, or sustained release; or a combination thereof.

Pharmaceutical Formulations—Forms

Formulations may suitably be in the form of liquids, solutions (e.g., aqueous, non-aqueous), suspensions (e.g., aqueous, non-aqueous), emulsions (e.g., oil-in-water, water-in-oil), elixirs, syrups, electuaries, mouthwashes, drops, tablets (including, e.g., coated tablets), granules, powders, losenges, pastilles, capsules (including, e.g., hard and soft gelatin capsules), cachets, pills, ampoules, boluses, suppositories, pessaries, tinctures, gels, pastes, ointments, creams, lotions, oils, foams, sprays, mists, or aerosols.

Formulations may suitably be provided as a patch, adhesive plaster, bandage, dressing, or the like which is impregnated with drug and short-chain sphingolipid and optionally one or more other pharmaceutically acceptable ingredients, including, for example, penetration, permeation, and absorption enhancers. Formulations may also suitably be provided in a the form of a depot or reservoir. The formulation may be in the form of a liposome or other microparticulate which is designed to target the drug (e.g., amphiphilic drug) (e.g., anthracycline) (e.g., doxorubicin), for example, to a tumour. The short-chain sphingolipid formulation may be in the form of a non-vesicular structure, such as, for example, a micelle, a cochleate, or an emulsion.

Formulations suitable for oral administration (e.g., by ingestion) include liquids, solutions (e.g., aqueous, non-aqueous), suspensions (e.g., aqueous, non-aqueous), emulsions (e.g., oil-in-water, water-in-oil), elixirs, syrups, electuaries, tablets, granules, powders, capsules, cachets, pills, ampoules, boluses.

Formulations suitable for buccal administration include mouthwashes, lozenges, pastilles, as well as patches, adhesive plasters, depots, and reservoirs. Losenges typically comprise the active agents in a flavored basis, usually sucrose and acacia or tragacanth. Pastilles typically comprise the active agents in an inert matrix, such as gelatin and glycerin, or sucrose and acacia. Mouthwashes typically comprise the active agents in a suitable liquid carrier.

Formulations suitable for sublingual administration include tablets, losenges, pastilles, capsules, and pills.

Formulations suitable for oral transmucosal administration include liquids, solutions (e.g., aqueous, non-aqueous), suspensions (e.g., aqueous, non-aqueous), emulsions (e.g., oil-in-water, water-in-oil), mouthwashes, losenges, pastilles, as well as patches, adhesive plasters, depots, and reservoirs.

Formulations suitable for non-oral transmucosal administration include liquids, solutions (e.g., aqueous, non-aqueous), suspensions (e.g., aqueous, non-aqueous), emulsions (e.g., oil-in-water, water-in-oil), suppositories, pessaries, gels, pastes, ointments, creams, lotions, oils, as well as patches, adhesive plasters, depots, and reservoirs.

Formulations suitable for transdermal administration include gels, pastes, ointments, creams, lotions, and oils, as well as patches, adhesive plasters, bandages, dressings, depots, and reservoirs.

Formulations suitable for intranasal administration, where the carrier is a liquid, include, for example, nasal spray, nasal drops, or by aerosol administration by nebuliser, include aqueous or oily solutions of the active agents.

Formulations suitable for intranasal administration, where the carrier is a solid, include, for example, those presented as a coarse powder having a particle size, for example, in the range of about 20 to about 500 microns which is administered in the manner in which snuff is taken, i.e., by rapid inhalation through the nasal passage from a container of the powder held close up to the nose.

Formulations suitable for pulmonary administration (e.g., by inhalation or insufflation therapy) include those presented as an aerosol spray from a pressurised pack, with the use of a suitable propellant, such as dichlorodifluoromethane, trichlorofluoromethane, dichoro-tetrafluoroethane, carbon dioxide, or other suitable gases.

Formulations suitable for ocular administration include eye drops wherein the active agents are dissolved or suspended in a suitable carrier, especially an aqueous solvent for the active agents.

Formulations suitable for rectal administration may be presented as a suppository with a suitable base comprising, for example, natural or hardened oils, waxes, fats, semi-liquid or liquid polyols, for example, cocoa butter or a salicylate; or as a solution or suspension for treatment by enema.

Formulations suitable for vaginal administration may be presented as pessaries, tampons, creams, gels, pastes, foams or spray formulations containing in addition to the active agents, such carriers as are known in the art to be appropriate.

Pharmaceutical Formulations—Parenteral Administration

In one embodiment, the pharmaceutical formulation is suitable for parenteral administration.

Formulations suitable for parenteral administration (e.g., by injection), include aqueous or non-aqueous, isotonic, pyrogen-free, sterile liquids (e.g., solutions, suspensions), in which the active agents are dissolved, suspended, or otherwise provided (e.g., in a liposome or other microparticulate). Such liquids may additionally contain other pharmaceutically acceptable ingredients, such as those described above, and more commonly anti-oxidants, buffers, preservatives, stabilisers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection. The formulations may be presented in unit-dose or multi-dose sealed containers, for example, ampoules and vials (e.g., a concentrated suspension for infusion), and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets.

Pharmaceutical Formulations—Liposomes

In an especially preferred embodiment, the pharmaceutical formulation is liposomal (i.e., is a liposomal pharmaceutical formulation).

In one embodiment, the pharmaceutical formulation is suitable for parenteral administration, and is liposomal.

The term "liposomal," as used herein, is intended to indicate that the drug (e.g., amphiphilic drug) (e.g., anthracycline) (e.g., doxorubicin) and short-chain sphingolipid are present in the form of a liposome (i.e., are liposome-entrapped).

In one embodiment, the pharmaceutical formulation is an aqueous, isotonic, pyrogen-free, sterile suspension of liposomes comprising the drug (e.g., amphiphilic drug) (e.g., anthracycline) (e.g., doxorubicin) and a short-chain sphingolipid (e.g., a short-chain glycosphingolipid or a short-chain sphingomyelin) (e.g., N-octanoyl-glucosylceramide, referred to as $C_8$-GlcCer) (e.g., N-hexanoyl-sphingomyelin, referred to herein as $C_6$-SM), suitable for parenteral administration.

In one embodiment, the liposomes are long-circulating liposomes (e.g., with a half life that is from 0.2 to 5 times the half-life of Caelyx®).

Liposomes

Liposomes (also called lipid vesicles) are aqueous compartments enclosed by a lipid bilayer (as in monolamellar liposomes) or many concentric bilayers (as in multilamellar liposomes). Lipids may be formed, for example, by suspending a suitable lipid (a vesicle-forming lipid), such as phosphatidyl choline, in an aqueous medium, and then sonicating (i.e., agitating by high frequency sound waves) to give a dispersion of closed vesicles. When prepared in this way, the liposomes are quite uniform in size, nearly spherical, and have a diameter of about 100 nm. Larger vesicles (on the order of 1 μm) can be prepared by slowly evaporating the organic solvent from a suspension of phospholipid in a mixed solvent system.

Suitable vesicle-forming lipids include amphipathic lipids having hydrophobic and polar head group moieties, and which (a) can form (spontaneously) into bilayer vesicles in water, as exemplified by phospholipids, or (b) are stably incorporated into lipid bilayers, with its hydrophobic moiety in contact with the interior, hydrophobic region of the bilayer membrane, and its polar head group moiety oriented toward the exterior, polar surface of the membrane.

Vesicle-forming lipids of this type are preferably ones having two hydrocarbon chains, typically acyl chains, and a polar head group. Examples of this class are the phospholipids, such as phosphatidylcholine (PC) (e.g., fully hydrogenated soy phosphatidylcholine (HSPC)), phosphatidylethanolamine (PE), phosphatidic acid (PA), phosphatidylglycerol (PG), phosphatidylinositol (PI), and sphingomyelin (SM), where the two hydrocarbon chains are typically between about 14-22 carbon atoms in length, and have varying degrees of unsaturation. Some preferred lipids are dipalmitoyl-phosphatidylcholine (DPPC), DSPC (distearoyl phosphatidylcholine), and distearyl-phosphatidylethanolamine (DSPE). The above-described lipids and phospholipids whose acyl chains have a variety of degrees of saturation can be obtained commercially, or prepared according to published methods.

Generally, liposomes comprise 20-99% by weight of vesicle-forming lipids. In some cases, where other lipids are also present, the upper limit is less, e.g., 20-70%, etc.

Additionally, the liposomes may optionally include (non-vesicle forming lipids) that can stabilize a vesicle or liposome composed predominantly of phospholipids. The most frequently employed lipid from this group is cholesterol (CH), typically at 25-40 mol %. Below about 20 mol % cholesterol in a bilayer, separate domains exist containing cholesterol and phospholipids and pure phospholipid (see, e.g., Mabrey). These bilayers show an increased permeability to water (see, e.g., Tsong). At mole percentages above 50% cholesterol starts destabilizing the bilayer. In some cases, other lipids, such as sitosterol, may be used in addition to, or as an alternative to, cholesterol.

Liposomes may additionally comprise vesicle-forming lipids (such as those described above) which are derivatized with a polymer chain. Vesicle-forming lipids with diacyl chains, such as phospholipids, are preferred. One exemplary phospholipid is phosphatidylethanolamine (PE) with a reactive amino group which is convenient for coupling to the activated polymers. An exemplary PE is distearyl PE (DSPE). The preferred polymer in the derivatized lipid, is polyethyleneglycol (PEG), preferably as a PEG chain having a molecular weight of 1,000-10,000 Da, more preferably 2,000-5,000 Da. Once a liposome is formed, the PEG chains provide a surface coating of hydrophilic chains sufficient to extend the blood circulation time of the liposomes in the absence of such a coating. Other hydrophilic polymers which may be suitable include polyvinylpyrrolidone, polymethyloxazoline, polyethyloxazoline, polyhydroxypropyl methacrylamide, polymethacrylamide, polydimethylacrylamide, polylactic acid, polyglycolic acid, and derivatized celluloses, such as hydroxymethylcellulose and hydroxyethylcellulose, and amino acid based polymers. Lipid-polymer conjugates containing these polymers attached to a suitable lipid, such as PE, have been described previously (see, e.g., Zalipsky et al., 1995; Allen et al., 1996; Woodle et al., 1991). The polymer-derivatized lipid, if present, is typically present in an amount of 1-20 mol % (e.g., 1-10 mol %) (e.g., 1-5 mol %).

An example of a preferred vesicle-forming lipid which is derivatized with a polymer chain are: N-(carbonyl-methoxy-polyethylene glycol 2000)-1,2-distearoyl-sn-glycero-3-phosphoethanolamine sodium salt (MPEG2000-DSPE) (e.g., STEALTH® liposomes, as found in Caelyx® and Doxil®).

Note such derivatized polymers are not always necessary or desired: the commercial product Daunoxome® (liposomal daunorubicin) is formulated in the form of relatively small (e.g., <100 nm) long-circulating liposomes using DSPC.

Liposomes may additionally comprise vesicle-forming lipids which have been modified for coupling antibody molecules to the liposome outer surface. These modified lipids may be of different types. In one embodiment, the modified lipid may contain a hydrophilic polymer spacer chain attached to the lipid. The hydrophilic polymer is typically end-functionalized for coupling antibody to its functionalized end.

The functionalized end group is preferably a maleimide group for selective coupling to antibody sulfhydryl groups. Other functionalized end groups include bromoacetamide and disulfide groups for reaction with antibody sulfhydryl groups, activated ester and aldehyde groups for reaction with antibody amine groups. Hydrazide groups are reactive toward aldehydes, which can be generated on numerous biologically relevant compounds. Hydrazides can also be acylated by active esters or carbodiimide-activated carboxyl groups. Acyl azide groups reactive as acylating species can be easily obtained from hydrazides and permit the attachment of amino containing ligands.

Again, a preferred polymer in the derivatized lipid, is polyethylene glycol (PEG). Other hydrophilic polymers which may be suitable for lipid derivatization include end-functionalized polyvinylpyrrolidone, polymethyloxazoline, polyethyloxazoline, polyhydroxypropyl methacrylamide, polymethacrylamide, polydimethylacrylamide, polylactic acid, polyglycolic acid, and derivatized celluloses, such as hydroxymethylcellulose and hydroxyethylcellulose, and amino acid based polymers. This polymer spacer chain is preferably shorter than the polymer chain described for the liposome surface polymer coating layer. For example, in a liposome composition containing a layer formed by PEG polymers of 2,000-5,000 Da, the spacer arm is generally of 100-5,000 Da, preferably 600-4,000 Da.

Liposomes may additionally comprise vesicle forming lipids which have been modified by a biotin molecule. To attach the antibody molecule to the biotinylated liposome surface, once the liposome is formed, the antibody molecule is also modified with biotin and then incubated in the presence of the avidin. Biotinylated lipids, such as biotinylated PE, are commercially available.

More generally, lipids may be modified by a substrate for use in binding a targeting molecule to a liposome surface. Typically, substrates, as exemplified with biotin, are relatively small, e.g., less than about 5,000 Da, to allow their incorporation into multilamellar liposomes with a minimum of disruption of the lipid bilayer structures. The substrate is preferably one capable of binding irreversibly to a targeting molecule, to ensure that the targeting molecule remains bound to the liposomes over its lifetime in the bloodstream.

In addition, the liposome formulation may include targeting-enhancing features, such as targeting ligands, for example, monoclonal antibodies, peptides, antibody fragments, (recombinant) proteins, growth factors, folate, carbohydrates, etc. See, e.g., Park et al., 2002; Pan et al., 2003; Koning et al., 1999; Koning et al., 2003.

Liposome-Entrapped Drug and Short-Chain Sphingolipid

In the liposomal pharmaceutical formulations described herein, the drug (e.g., amphiphilic drug) (e.g., anthracycline) (e.g., doxorubicin) and the short-chain sphingolipid (e.g., short-chain glycosphingolipid or short-chain sphingomyelin) (e.g., N-octanoyl-glucosylceramide, referred to as $C_8$-GlcCer) (e.g., N-hexanoyl-sphingomyelin, referred to herein as $C_6$-SM) are liposome-entrapped.

In one embodiment, at least 70% of the drug is liposome-entrapped.

In one embodiment, at least 80% of the drug is liposome-entrapped.

In one embodiment, at least 80% of the drug is liposome-entrapped.

In one embodiment, at least 70% of the short-chain sphingolipid is liposome-entrapped.

In one embodiment, at least 80% of the short-chain sphingolipid is liposome-entrapped.

In one embodiment, at least 80% of the short-chain sphingolipid is liposome-entrapped.

Each of these components may be tend to partition into the aqueous compartment of liposome, or into the lipid bilayer phase of the liposome (membrane-entrapped).

For example, it is believed that the short-chain sphingolipid is predominantly membrane-entrapped, while the drug (e.g., amphiphilic drug) (e.g., anthracycline) (e.g., doxorubicin) is predominantly partitioned into the aqueous compartment.

Liposomes—Methods of Preparation

Liposomes may be prepared by a variety of well known techniques (see, e.g., Szoka et al., 1980). Multilamellar vesicles (MLVs) can be formed by simple lipid-film hydration techniques. In this procedure, a mixture of liposome-forming lipids dissolved in a suitable organic solvent is evaporated in a vessel to form a thin film, which is then covered by an aqueous medium. The lipid film hydrates to form MLVs, typically with sizes of 0.1-10 µm. In an alternative method, liposomes are prepared by vortexing dried lipid films in a buffered aqueous solution (see, e.g., Olson).

Generally, the drug (e.g., amphiphilic drug) (e.g., anthracycline) (e.g., doxorubicin) is incorporated into liposomes by adding it to the vesicle-forming lipids prior to liposome formation, as described below, to entrap the drug in the formed liposome. If the drug is hydrophobic, it may be added directly to the hydrophobic mixture. If the drug is hydrophilic, it may be added to the aqueous medium which covers the thin film of evaporated lipids.

Alternatively, the drug (e.g., amphiphilic drug) (e.g., anthracycline) (e.g., doxorubicin) may be incorporated into preformed liposomes by active transport mechanisms. Typically, in this case drug is taken up in liposomes in response to a potassium or hydrogen or ammonium sulfate or metal ion concentration differential (see, e.g., Mayer, 1986; Mayer, 1989; Haran et al., 1993; Lasic et al., 1995; Cheung et al., 1998; Abraham et al., 2002).

One effective sizing method for REVs and MLVs involves extruding an aqueous suspension of the liposomes through a series of polycarbonate membranes having a selected uniform pore size in the range of 0.03 to 0.2 µm, typically 0.05, 0.08, 0.1, or 0.2 µm. The pore size of the membrane corresponds roughly to the largest sizes of liposomes produced by extrusion through that membrane, particularly where the preparation is extruded two or more times through the same membrane. Homogenization methods are also useful for down-sizing liposomes to sizes of 100 nm or less (see, e.g., Martin, 1990).

Some Preferred Liposomal Pharmaceutical Formulations

In one embodiment, the liposomes of the liposomal pharmaceutical formulation are prepared using a mixture of lipids comprising, at least, vesicle-forming lipids and a short-chain sphingolipid (e.g., a short-chain glycosphingolipid or a short-chain sphingomyelin) (e.g., N-octanoyl-glucosylceramide, referred to as $C_8$-GlcCer) (e.g., N-hexanoyl-sphingomyelin, referred to herein as $C_6$-SM), as described herein.

In one embodiment, the mixture of lipids comprises phospholipids and a short-chain sphingolipid, as described herein.

In one embodiment, the mixture of lipids additionally comprises cholesterol.

In one embodiment, the mixture of lipids comprises phospholipids, cholesterol, and a short-chain sphingolipid, as described herein.

In one embodiment, the mixture of lipids comprises phosphatidylcholines, cholesterol, and a short-chain sphingolipid, as described herein.

In one embodiment, the mixture of lipids comprises fully hydrogenated soy phosphatidylcholine (HSPC), cholesterol, and a short-chain sphingolipid, as described herein.

In one embodiment, the mixture of lipids comprises dipalmitoyl-phosphatidylcholine (DPPC), cholesterol, and a short-chain sphingolipid, as described herein.

In one embodiment, the mixture of lipids additionally comprises a vesicle-forming lipid which is derivatized with a polymer chain.

In one embodiment, the mixture of lipids additionally comprises a phosphatidylethanolamine (PE) which is derivatized with polyethyleneglycol (PEG).

In one embodiment, the mixture of lipids additionally comprises N-(carbonyl-methoxypolyethylene glycol 2000)-1,2-distearoyl-sn-glycero-3-phosphoethanolamine sodium salt (MPEG2000-DSPE).

In one embodiment, the amount of short-chain sphingolipid is an effective amount; e.g., an amount which is sufficient to increase drug (e.g., amphiphilic drug) (e.g., anthracycline) (e.g., doxorubicin) uptake, e.g., by 20%; 30%; 40%; 50%; 100%; a factor of 2; a factor of 3.

In one embodiment, the amount of short-chain sphingolipid (e.g., short-chain glycosphingolipid or short-chain sphingomyelin) (e.g., N-octanoyl-glucosylceramide, referred to as $C_8$-GlcCer) (e.g., N-hexanoyl-sphingomyelin, referred to herein as $C_6$-SM) is 0.5-50 mol %; 1-25 mol %; 1-20 mol %; 1-15 mol %; 1-10 mol %; 2-20 mol %; 2-15 mol %; 2-10 mol %; 3-20 mol %; 3-15 mol %; 3-10 mol %.

In one embodiment, the amount of cholesterol is 20-50 mol %; 25-50 mol %; 25-45 mol %; 25-40 mol %; 30-50 mol %; 30-45 mol %; 30-40 mol %; 35-45 mol %; 40%.

In one embodiment, the amount of phospholipid (e.g., phosphatidylcholine) (e.g., fully hydrogenated soy phosphatidylcholine (HSPC)) (e.g., dipalmitoyl-phosphatidylcholine (DPPC)), excluding phospholipid which is derivatized with a polymer chain, if present, is 45-70 mol %; 35-75 mol %; 40-70 mol %; 45-65 mol %; 45-60 mol %; 50-65 mol %; 55 mol %.

In one embodiment, the amount of vesicle-forming lipid which is derivatized with a polymer chain (e.g., MPEG2000-DSPE), if present, is 1-15 mol %; 1-10 mol %; 1-7 mol %; 1-5 mol %; 2-10 mol %; 2-7 mol %; 2-5 mol %; 3-10 mol %; 3-7 mol %; 5 mol %.

In one embodiment, the molar ratio of the amount of short-chain sphingolipid to the amount of phospholipid (excluding phospholipid which is derivatized with a polymer chain, if present), is from 0.05 to 1; from 0.1 to 0.5; from 0.2 to 0.4.

In one embodiment, the molar ratio of the amount of cholesterol, if present, to the amount of phospholipid (excluding phospholipid which is derivatized with a polymer chain, if present), is from 0.1 to 0.5; from 0.2 to 0.4.

In one embodiment, the molar ratio of the amount of vesicleforming lipid which is derivatized with a polymer chain, if present, to the amount of phospholipid (excluding phospholipid which is derivatized with a polymer chain, if present) is from 0.1 to 0.5; from 0.2 to 0.4.

In one embodiment, the molar ratio of the amount of cholesterol, if present, to the amount of vesicle-forming lipid which is derivatized with a polymer chain, if present, is from 0.8 to 1.2. In one embodiment, the liposomes of the liposomal pharmaceutical formulation comprise 0.05-0.50 µmol anthracycline (e.g., doxorubicin) per µmol phospholipid. In one embodiment, the amount is 0.10-0.40 µmol/µmol; 0.10-0.35 µmol/µmol; 0.10-0.30 µmol/µmol; 0.15-0.40 µmol/µmol; 0.15-0.35 µmol/µmol; 0.15-0.30 µmol/µmol; 0.20-0.40 µmol/µmol; 0.20-0.35 µmol/µmol; 0.20-0.30 µmol/µmol.

In one embodiment, the pharmaceutical formulation is a (concentrated) liposomal pharmaceutical formulation (suitable for parenteral infusion) having a doxorubicin concentration of 2 mg/mL.

The liposomes may additionally comprise other pharmaceutically acceptable ingredients, such as ammonium sulfate, histidine (as buffer), hydrochloric acid and/or sodium hydroxide (for pH control), sucrose (to maintain isotonicity), and water-for-injection.

In one embodiment, the liposomes have a mean diameter of:

30 to 500 nm; 30 to 300 nm; 30 to 200 nm; 30 to 150 nm; 30 to 120 nm;
50 to 500 nm; 50 to 300 nm; 50 to 200 nm; 50 to 150 nm; 50 to 120 nm;
70 to 500 nm; 70 to 300 nm; 70 to 200 nm; 70 to 150 nm; 70 to 120 nm.

Each compatible combination of the above features is also included as if it was explicitly recited.

In one embodiment, the liposomes are Caelyx® or Doxil® liposomes which have been treated with a short-chain sphingolipid, as described herein.

Methods of Making Linosomal Pharmaceutical Formulations

One aspect of the present invention pertains to a method of making a liposomal pharmaceutical formulation comprising the steps of:
(a) forming a lipid mixture, as described above (e.g., comprising, at least, vesicle-forming lipids and a short-chain sphingolipid);
(b) forming liposomes from said lipid mixture; and
(c) adding a drug (e.g., an amphiphilic drug) (e.g., an anthracycline) (e.g., doxorubicin) to the liposomes formed in (b); thereby forming liposome-entrapped drug.

One aspect of the present invention pertains to a method of making a liposomal pharmaceutical formulation comprising the steps of:
(a) forming a lipid mixture, as described above (e.g., comprising, at least, vesicle-forming lipids and a short-chain sphingolipid);
(b) adding a drug (e.g., an amphiphilic drug) (e.g., an anthracycline) (e.g., doxorubicin) to said lipid mixture;
(c) forming liposomes from the mixture formed in (b); thereby forming liposome-entrapped drug.

Uses

The pharmaceutical formulations (and their drug and short-chain sphingolipid components), as described herein, are useful in the treatment of proliferative conditions, such as, for example, cancer, for example, ovarian cancer, Kaposi's syndrome, AIDS-related Kaposi's syndrome. Therefore, they may also be referred to as "anti-proliferative" or "anti-cancer" pharmaceutical formulations.

One of ordinary skill in the art is readily able to determine whether or not a candidate pharmaceutical formulation treats a proliferative condition (e.g., cancer) for any particular cell type. For example, assays which may conveniently be used to assess the activity offered by a particular compound are well known, and some are described in the examples below.

One aspect of the present invention pertains to a method of increasing the bioavailability (and/or the cellular uptake) of a drug (e.g., an amphiphilic drug) (e.g., an anthracycline) (e.g., doxorubicin), which method includes the step of co-administering said drug with a short-chain sphingolipid (e.g., a short-chain glycosphingolipid or a short-chain sphingomyelin) (e.g., N-octanoyl-glucosylceramide, referred to as $C_8$-GlcCer) (e.g., N-hexanoyl-sphingomyelin, referred to herein as $C_6$-SM), as described herein.

In one embodiment, the drug and short-chain sphingolipid are co-administered at the same time, as components of single pharmaceutical formulation.

In one embodiment, the drug and short-chain sphingolipid are co-administered at (approximately) the same time, but as components of separate pharmaceutical formulations.

In one embodiment, the drug and short-chain sphingolipid are co-administered at different times, but as components of separate pharmaceutical formulations.

Use in Methods of Treatment

One aspect of the present invention pertains to a method for the treatment of a proliferative condition (e.g., cancer), comprising administering to a subject suffering from said condition a therapeutically-effective amount of a pharmaceutical formulation, as described herein.

Use in Methods of Therapy

One aspect of the present invention pertains to a pharmaceutical formulation, as described herein, for use in a method of treatment of the human or animal body by therapy.

One aspect of the present invention pertains to a pharmaceutical formulation, as described herein, for use in a method of treatment of a proliferative condition (e.g., cancer) of the human or animal body by therapy.

Use in the Manufacture of Medicaments

One aspect of the present invention pertains to use of an anti-proliferative drug (e.g., an anthracycline) (e.g., doxorubicin), as described herein, and a short-chain sphingolipid (e.g., a short-chain glycosphingolipid or a short-chain sphingomyelin) (e.g., N-octanoyl-glucosylceramide, referred to as $C_8$-GlcCer) (e.g., N-hexanoyl-sphingomyelin, referred to herein as $C_6$-SM), as described herein, for the manufacture of a medicament for use in the treatment of a proliferative condition (e.g., cancer).

Antiproliferative and Anticancer Applications

The pharmaceutical formulations described herein are useful in the treatment of proliferative conditions, such as, for example, cancer, for example, ovarian cancer, Kaposi's syndrome, AIDS-related Kaposi's syndrome.

The terms "cell proliferation," "proliferative condition," "proliferative disorder," and "proliferative disease," are used interchangeably herein and pertain to an unwanted or uncontrolled cellular proliferation of excessive or abnormal cells which is undesired, such as, neoplastic or hyperplastic growth, whether in vitro or in vivo.

Examples of proliferative conditions include, but are not limited to, benign, pre-malignant, and malignant cellular proliferation, including but not limited to, neoplasms and tumours (e.g., histocytoma, glioma, astrocytoma, osteoma), cancers (e.g., lung cancer, small cell lung cancer, gastrointestinal cancer, bowel cancer, colon cancer, breast carcinoma, ovarian carcinoma, prostate cancer, testicular cancer, liver cancer, kidney cancer, bladder cancer, pancreas cancer, spleen cancer, brain cancer, sarcoma, osteosarcoma, Kaposi's sarcoma, AIDS-related Kaposi's sarcoma, skin cancer, melanoma, thyroid gland cancer, adrenal gland cancer, pituitary gland cancer, leukemias, lymphomas), psoriasis, bone diseases, fibroproliferative disorders (e.g., of connective tissues), and atherosclerosis.

In one embodiment, the drug is doxorubicin or a salt (e.g., acid addition salt) thereof; and the proliferative condition is a proliferative condition that is treated by (e.g., treatable by) (e.g., known to be treated by) (e.g., known to be treatable by) doxorubicin.

In one embodiment, the proliferative condition is cancer.

In one embodiment, the drug is doxorubicin or a salt (e.g., acid addition salt) thereof; and the proliferative condition is cancer that is treated by (e.g., treatable by) (e.g., known to be treated by) (e.g., known to be treatable by) doxorubicin.

In one embodiment, the proliferative condition is ovarian cancer, Kaposi's syndrome, or AIDS-related Kaposi's syndrome.

Treatment

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, regression of the condition, amelioration of the condition, and cure of the condition. Treatment as a prophylactic measure (i.e., prophylaxis, prevention) is also included.

The term "therapeutically-effective amount," as used herein, pertains to that amount of an active compound, or a material, composition or dosage from comprising an active compound, which is effective for producing some desired therapeutic effect, commensurate with a reasonable benefit/risk ratio, when administered in accordance with a desired treatment regimen.

The term "treatment" includes combination treatments and therapies, in which two or more treatments or therapies are combined, for example, sequentially or simultaneously. Examples of treatments and therapies include, but are not limited to, chemotherapy (the administration of active agents, including, e.g., drugs, antibodies (e.g., as in immunotherapy), prodrugs (e.g., as in photodynamic therapy, GDEPT, ADEPT, etc.); surgery; radiation therapy; and gene therapy. For example, active compounds, as described above, may also be used in combination therapies, for example, in conjunction with other agents, for example, cytotoxic agents.

Routes of Administration

The formulation may be administered to a subject by any convenient route of administration, whether systemically/peripherally or topically (i.e., at the site of desired action).

Routes of administration include, but are not limited to, oral. (e.g., by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

In one embodiment, the formulation is administered parenterally.

The Subject (Patient)

The subject may be an animal, a chordate, a vertebrate, a mammal, a placental mammal, a marsupial (e.g., kangaroo, wombat), a monotreme (e.g., duckbilled platypus), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutang, gibbon), or a human.

The subject may be any of its forms of development, for example, a foetus.

In one embodiment, the subject (patient) is a human.

Dosage

It will be appreciated by one of skill in the art that appropriate dosages can vary from patient to patient. Determining the optimal dosage will generally involve the balancing of the level of therapeutic benefit against any risk or deleterious side effects. The selected dosage level will depend on a variety of factors including, but not limited to, the activity of the particular compound(s), the route of administration, the time of administration, the rate of excretion of the compound(s), the duration of the treatment, other drugs, compounds, and/or materials used in combination, the severity of the condition, and the species, sex, age, weight, condition, general health, and prior medical history of the patient. The amount and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

Where the drug is a salt, an ester, an amide, a prodrug, or the like, the amount administered is calculated on the basis of the parent drug and so the actual weight to be used is increased proportionately.

Appropriate dosages for the known drugs (e.g., amphiphilic drugs) (e.g., anthracyclines) (e.g., doxorubicin) are known. Examples of suitable dosages include: doxorubicin: 60-75 mg/m$^2$; epirubicin: 60-120 mg/m$^2$; and daunorubicin: 25-45 mg/M$^2$. Dosages above about 550 mg/M$^2$ doxorubicin may lead to irreversible myocardial toxicity leading to congestive heart failure often unresponsive to cardiac support therapy.

In one embodiment, the pharmaceutical formulation is a (concentrated) liposomal pharmaceutical formulation, suitable for parenteral infusion, having a doxorubicin concentration of 1-3 mg/mL; about 2 mg/mL.

Other Uses

Pharmaceutical formulations, as described herein, may also be used as cell culture additives, for example, to inhibit cell proliferation.

Pharmaceutical formulations, as described herein, may also be used as part of an in vitro assay, for example, in order to determine whether a candidate host is likely to benefit from treatment with the pharmaceutical formulation in question.

Pharmaceutical formulations, as described herein, may also be used as a standard, for example, in an assay, in order to identify other antiproliferative agents, anticancer agents, etc.

Kits

One aspect of the invention pertains to a kit comprising (i) a pharmaceutical composition, as described herein, preferably provided in a suitable container and/or with suitable packaging; and (ii) instructions for use, for example, written instructions on how to administer the pharmaceutical formulation, etc.

The written instructions may also include a list of indications for which the active ingredient is a suitable treatment.

One aspect of the invention pertains to a kit comprising (i) (a) a drug (e.g., an amphiphilic drug) (e.g., an anthracycline) (e.g., doxorubicin) and (b) a short-chain sphingolipid (e.g., a short-chain glycosphingolipid or a short-chain sphingomyelin) (e.g., N-octanoyl-glucosylceramide, referred to as $C_8$-GlcCer) (e.g., N-hexanoyl-sphingomyelin, referred to herein as $C_6$-SM), as described herein, preferably provided in a suitable container and/or with suitable packaging; and (ii) instructions for use, for example, written instructions on how to prepare (and optionally administer) a pharmaceutical formulation, as described herein.

One aspect of the invention pertains to a kit comprising (i) (a) a drug (e.g., an amphiphilic drug) (e.g., an anthracycline) (e.g., doxorubicin); (b) a short-chain sphingolipid (e.g., a short-chain glycosphingolipid or a short-chain sphingomyelin) (e.g., N-octanoyl-glucosylceramide, referred to as $C_8$-GlcCer) (e.g., N-hexanoyl-sphingomyelin, referred to herein as $C_6$-SM), as described herein; (c) optionally one or more vesicle-forming lipids (e.g., a phospholipid); and (d) optionally cholesterol, preferably provided in a suitable container and/or with suitable packaging; and (ii) instructions for use, for example, written instructions on how to prepare (and optionally administer) a liposomal pharmaceutical formulation, as described herein.

If appropriate, the kit may optionally including appropriate reagents (e.g., buffers, solvents) and devices (e.g., tubes, syringes) for assembly and use (e.g., administration).

EXAMPLES

The following are examples are provided solely to illustrate the present invention and are not intended to limit the scope of the invention, as described herein.

Materials

A431 cells were obtained from the American Type Culture Collection (Manassas Va., USA).

Dipalmitoyl-phosphatidylcholine (DPPC) and pegylated distearyl-phosphatidylethanolamine (MPEG2000-DSPE) were obtained from Lipoid (Ludwigshafen, Germany).

$C_8$-GlcCer was obtained from Avanti Polar Lipids (Alabastar Ala., USA).

Polycarbonate filters were obtained from GE Osmonics (Minnetonka Minn., USA).

PD-10 Sephadex columns were obtained from Pharmacia (Upsala, Sweden).

Doxorubicin.HCl was obtained from Pharmachemie (Haarlem, The Netherlands).

Caelyx® was obtained from Schering-Plough (Heist-op-den-Berg, Belgium).

Cholesterol, bicinchoninic acid (BCA) protein kit, 3-[4,5-dimethylthiazol-2-yl]-2,5-diphenyl tetrazolium bromide (MTT) and Dowex® 50WX4-400 resin (Dowex) were obtained from Sigma (St. Louis Mo., USA).

LK6D silica TLC plates were obtained from Whatman (Maidstone, UK).

Vectashield mounting medium was obtained from Vector Laboratories (Burlingame Calif., USA).

The CytoTox 96 lactate dehydrogenase (LDH) activity kit was obtained from Promega (Madison Wis., USA).

Methods

Liposome Preparation and Analysis

Liposomes were prepared by lipid film hydration, extrusion, and remote loading (see, e.g., Haran et al., 1993). Mixtures of DPPC, cholesterol, MPEG2000-DSPE and $C_8$-GlcCer were prepared in ethanol, in various molar ratios (See Table 1). A lipid film was created under reduced pressure on a rotary evaporator, and dried under a stream of nitrogen. Liposomes were formed by addition of 250 mM ammonium sulfate to the remaining lipid film. This hydrated lipid dispersion was then sized by extrusion through, successively, 200 nm (3 passes), 100 nm (3 passes), and double 50 nm (6 passes) polycarbonate filters. Non-encapsulated ammonium sulfate was removed by gel permeation chromatography, using a PD-10 Sephadex column eluted with 123 mM citrate buffer, pH 5.5. For liposomal doxorubicin loading, the drug was added in a molar ratio of doxorubicin to total lipid of 1:5, and incubated for 1 hour at 55° C. (see, e.g., Haran et a., 1993). Non-encapsulated doxorubicin was then removed by gel permeation chromatography, using a PD-10 Sephadex column eluted with 135 mM NaCl in 10 mM Hepes, pH 7.4.

For post-insertion of $C_8$-GlcCer into Caelyx®, the liposomes were incubated (30 minutes at 37° C.) with various concentrations of the lipid (0, 66, 132, 220, 330, 440 µM), which was added as an ethanolic solution (never exceeding 2% v/v). Liposomes were then subjected to ultra-centrifugation in a Kontron TFT 80.2 rotor (70,000 rpm, 1 hour at 20° C.), and pellets were washed with 135 mM NaCl in 10 mM Hepes, pH 7.4.

Total phospholipid phosphorus of each liposomal preparation was determined by a phosphate assay (see, e.g., Rouser et al., 1970). For confirmation of $C_8$-GlcCer incorporation and post-insertion, lipids were extracted from the liposomes (see, e.g., Bligh and Dyer, 1959). Extracts were then applied to a 60 Angstrom silica gel TLC plate, which was developed in chloroform/methanol/water (60:30:8, by vol.). Lipids were visualized by iodine vapor staining, and $C_8$-GlcCer was identified with the aid of a standard that was run on the same plate. Final liposomal doxorubicin contents were established fluorometrically, after solubilization of the liposomes in 1% (w/v) Triton X-100, by comparison to standard amounts. Particle size and size distribution were determined by dynamic laser light scattering, using a Malvern 4700 system equipped with a 75 mW argon laser. Data analysis was performed with Malvern Automeasure software (Version 3.2). To establish the extent of doxorubicin leakage, liposomes were stored for various periods of time and at various temperatures (see Table 1). Samples were then subjected to ultra-centrifugation, as described, and doxorubicin was measured in aliquots of the supernatants.

TABLE 1

|  | $C_8$-GlcCer-enriched liposomes | | | | | | Caelyx ® | empty controls | |
| --- | --- | --- | --- | --- | --- | --- | --- | --- | --- |
| DPPC (mol %) | 62 | 60 | 58 | 56 | 53 | 50 | 55 | 62 | 50 |
| cholesterol (mol %) | 33 | 32 | 31 | 30 | 29 | 28 | 40 | 33 | 28 |
| MPEG2000-DSPE (mol %) | 5 | 5 | 5 | 5 | 5 | 5 | 5 | 5 | 5 |
| C8-GlcCer (mol %) | 0 | 3 | 6 | 9 | 13 | 17 | 0 | 0 | 17 |
| doxorubicin (µmol/µmol phospholipid) | 0.23 | 0.27 | 0.28 | 0.26 | 0.28 | 0.26 | 0.29 | — | — |
| diameter (nm) | 107 | 104 | 104 | 107 | 108 | 99 | 85 | 106 | 99 |
| leakage (% loss after 1 day at 37° C.) | 0.35 | 0.14 | 0.25 | 0.33 | 0.37 | 0.24 | 0.57 | — | — |

TABLE 1-continued

| | $C_8$-GlcCer-enriched liposomes | | | | | | Caelyx ® | empty controls |
|---|---|---|---|---|---|---|---|---|
| leakage (% loss after 60 days at 4° C.) | 0.46 | 0.66 | 0.56 | 0.49 | 0.44 | 0.48 | n.d. | — — |

Table 1 shows the composition and characteristics of the liposome preparations. Liposomes with various lipid compositions were prepared, as described above, and loaded with doxorubicin, or not (empty controls). For comparison, a commercially available liposomal doxorubicin preparation (Caelyx®) was also analyzed. Doxorubicin content of the preparations was measured and expressed as μmol per μmol of liposomal phospholipid. Mean liposome diameters were obtained from volume distribution curves, produced by a dynamic laser light scattering-based particle analyzer. Polydispersity is a measure for variation in particle size within the liposome population, and varies between 0 (complete monodispersity) and 1 (maximal variation). With polydispersities of 0.07 all present preparations fell well within acceptable limits of variation.

Cell Culture

A431 (adherent human epidermoid carcinoma cells) were cultured in Dulbecco's modified Eagle medium (DMEM), supplemented with 10% (v/v) fetal calf serum, 100 units/ml penicillin, 100 μg/ml streptomycin and 4 mM L-glutamine. Cells were sub-cultured once a week by trypsinization and maintained in a water-saturated atmosphere of 5% $CO_2$ at 37° C. All studies were performed at a confluency of 80-90%.

Cellular Doxorubicin Uptake

For cellular doxorubicin accumulation measurements, A431 cells were cultured in flat-bottom 96-well plates. At confluency, cells were changed to serum-free medium and exposed to 50 μM free or to 20 μM liposomal doxorubicin. After extensive washing, cells were lysed in 100 μl of 1% (w/v) Triton X-100. Native fluorescence intensities were then measured by a Perkin Elmer Victor Wallac II fluorescence microplate reader, using 485 nm and 535 nm filters for excitation and emission, respectively. All values were corrected for background fluorescence. Cellular doxorubicin contents were calculated with the aid of standard amounts, and corrected for differences in protein content, as determined with the BCA assay (see, e.g., Smith et al., 1985).

Microscopy

For microscopic studies, A431 cells were cultured on 0.5% (w/v) gelatin-coated glass coverslips. After exposure to liposomal doxorubicin, cells were washed, fixed (10 min in 4% (w/v) paraformaldehyde in PBS) and mounted in Vectashield on glass slides. All samples were examined with a Zeiss Axiovert S 100 inverted fluorescence microscope, employing a mercury lamp in combination with a filter set consisting of a 450-490 nm band pass excitation filter, a 510 nm beam splitter and a 520 nm long pass emission filter. Specimens were photographed through a 40× oil immersion objective by a Zeiss AxioCam CCD camera, using equal exposure times (1350 ms).

Membrane Leakage Assay

To investigate (loss of) plasma membrane integrity, the release of the cytosolic enzyme LDH into phenol red-free cell culture medium was monitored. Flat-bottom 96-well plates containing (liposome-treated) A431 cells were centrifuged (2000 rpm, 5 minutes at 20° C.) and 50 μl aliquots of the supernatants were assessed for LDH activity with the Cyto-Tox 96 kit, according to the manufacturer's instructions. Values obtained from cells that were lysed in 0.8% Triton X-100 served as positive control. All data were corrected for protein contents, as determined with the BCA assay (see, e.g., Smith et al., 1985).

Cell Viability

For viability assessment, A431 cells were cultured in flat-bottom 96-well plates. After experimental treatments, 100 μg of the mitochondrial dehydrogenase substrate MTT was added to each well (see, e.g., Carmichael et al., 1987). Cells were then incubated for 60 minutes at 37° C. After centrifugation (3000 rpm, 10 minutes at 4° C.) supernatants were removed. The precipitated blue formazan products were then dissolved in 100 μl DMSO, and absorbencies were read in a Bio-Tek Instruments EL 340 photospectrometric microplate reader at 540 nm. Background absorbencies were subtracted and values from wells containing untreated control cells were set at 100% viability.

Studies and Results

Low Toxicity of the Doxorubicin-uptake Enhancing Sphingolipid $C_8$-GlcCer

The inventors have found that the cellular uptake of free doxorubicin can be greatly enhanced in vitro, by co-addition of $C_6$-SM, a semi-synthetic short-chain sphingolipid analogue. In A431 human epidermoid carcinoma cells for example, 15 μM of co-administered $C_6$-SM increased the uptake of free doxorubicin to 461.8±126.9% (within an hour), as compared to 100% uptake under control conditions. At its effective low micromolar concentrations, and during short-term incubations, $C_6$-SM displays no toxic effects. During 1 hour incubation with 10 μM of the lipid for example, A431 cells released just 0.5±0.5% of total their total LDH activity, indicating that no plasma membrane damage occurred (cells treated with 0.8% Triton X-100 served as positive control, and were set at 100%). Furthermore, A431 cells fully retained their general viability under these conditions (95.6±19.1% of the cells were viable, as determined 24 hours after a 1 hour incubation with 10 μM of $C_6$-SM). However, much higher concentrations and/or longer incubation periods clearly induced toxic responses. For example, 100 μM $C_6$-SM caused substantial membrane damage (53.9±7.9% LDH release) and after a 24 hour exposure to 20 μM only 29.3±5.5% of the cells survived.

The inventors have now identified $C_8$-GlcCer as another sphingolipid analogue that exhibits strong doxorubicin uptake-enhancing properties (271.7±58.5% at 15 μM in A431 cells). Although slightly less potent than $C_6$-SM, this analogue is much less toxic, even at high concentrations and during prolonged incubation times. In the presence of 100 μM of $C_8$-GlcCer, A431 plasma membranes remained fully intact (0.0±0.6% LDH release), and general viability after 24 hour exposure to 20 μM $C_8$-GlcCer still reached 71.3±5.3%.

Further studies were performed to demonstrate that such glycosphingolipids retain their doxorubicin uptake-enhancing properties, when co-formulated within liposomal doxorubicin. Since liposomes have long circulation times and a high lipid-loading capacity, the low toxicity of glycosphingolipids such as $C_8$-GlcCer makes them the lipids of choice.

Characterization of $C_8$-GlcCer-enriched PEG-liposomes

A series of PEG-liposomes were prepared containing increasing mol % of $C_8$-GlcCer (see Table 1, above). Whereas the relative amounts of PEG-containing phospholipid (MPEG2000-DSPE) and cholesterol were kept constant, DPPC contents decreased in this series, to compensate for increasing mol % of $C_8$-GlcCer. Liposomes were loaded with doxorubicin as described (see, e.g., Haran et al., 1993). The lipid composition, doxorubicin loading efficiencies, size, and stability of the in-house prepared liposomes fully matched those of commercial PEG-liposomal doxorubicin (Caelyx®). Theoretically, truncated lipid analogues exhibit membrane-disturbing properties. To prevent liposomal instability, $C_8$-GlcCer contents were limited to 17 mol %. As indicated by a minimal loss through leakage (at 37° C. or during prolonged storage), all $C_8$-GlcCer-containing liposomes were stable.

Enhanced Cellular Doxorubicin Uptake from $C_8$-GlcCer-enriched Liposomes

Figure 2:
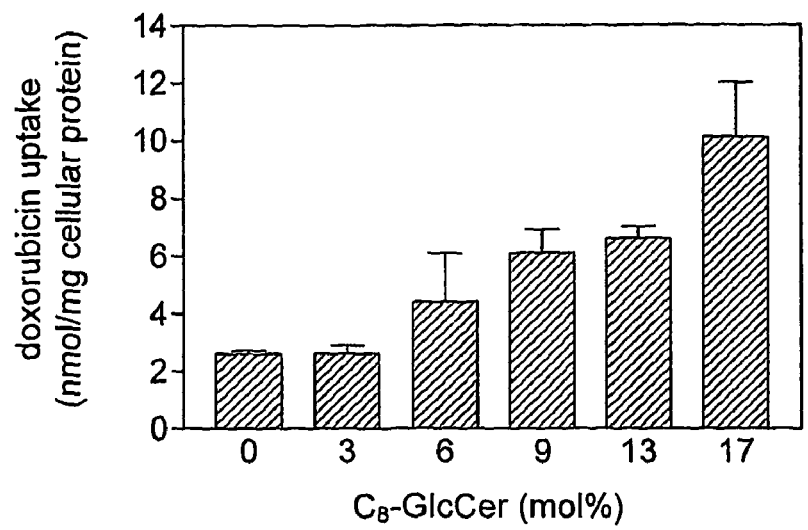
FIG. 2 is a bar-graph of doxorubicin uptake (nmol/mg cellular protein) for different concentrations (mol %) of $C_8$-GlcCer. A431 cells were changed to serum-free medium. Cells were then treated for 24 hours with doxorubicin-loaded PEG-liposomes, containing increasing mol % of $C_8$-GlcCer. The liposomal doxorubicin concentration in the culture medium was 20 µM. Unbound liposomes were washed away and cells were lysed. Employing its native fluorescence, doxorubicin was quantified fluorometrically by comparison to standard amounts. Values were corrected for cellular protein contents and expressed as mean±SD (n=3 independent experiments, each performed in 6-fold).
Figure 3:
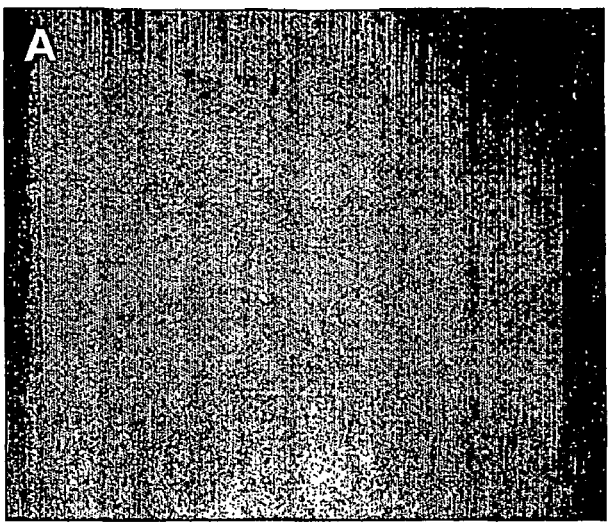
FIG. 3 is a series of photographs of cell samples. A431 cells were cultured on gelatin-coated coverslips and treated for 24 hours, under serum-free conditions, with buffer (A), with 20 µM doxorubicin as conventional PEG-liposomes (B), or as 17 mol % $C_8$-GlcCer-enriched PEG-liposomes (C). Final liposomal doxorubicin concentrations were 20 µM. Cells were washed, fixed in 4% (w/v) paraformaldehyde and mounted. Specimens were examined by fluorescence microscopy, using a filter set consisting of a 450-490 nm band pass excitation filter, a 510 nm beam splitter and a 520 nm long pass emission filter. Cells were photographed through a 40× oil immersion objective, using equal exposure times (1350 ms).
Figure 3:
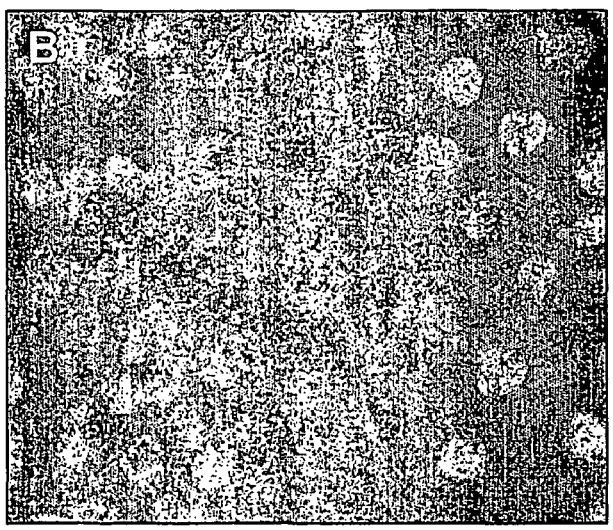
Figure 3:

When cultured A431 cells were incubated for 24 hours in the presence of normal PEG-liposomal doxorubicin, 2.6±0.1 nmol drug per mg of cellular protein accumulated in the cells (see FIG. 2). When using $C_8$-GlcCer-enriched liposomes however, this uptake increased up to 4-fold, at 17 mol % of the lipid analogue. This observation was confirmed by microscopy, making use of the native fluorescence of doxorubicin. In the absence of substantial background staining (see FIG. 3A), doxorubicin accumulated in cell nuclei during 24 hours incubation with liposomal doxorubicin (see FIG. 3B). Again, this was significantly enhanced when employing $C_8$-GlcCer-enriched liposomes (see FIG. 3C).

Improved Doxorubicin Delivery Results in Enhanced Cytotoxicity

Figure 4:
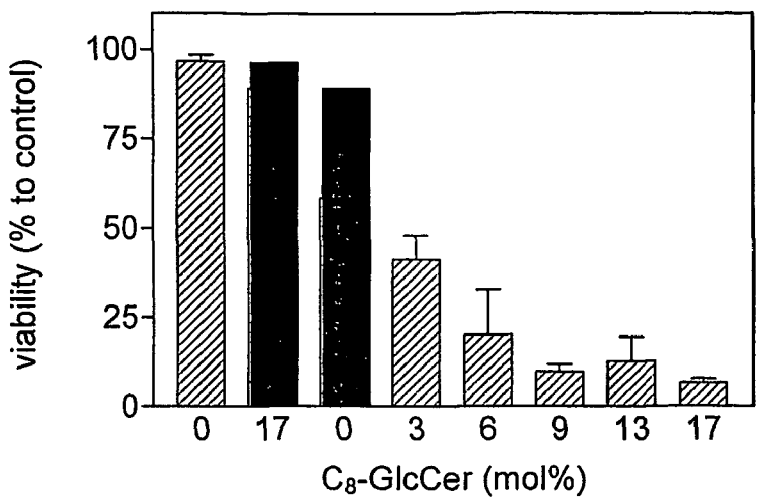
FIG. 4 is a bar-graph of cell viability (% to control) for different concentrations (mol %) of $C_8$-GlcCer. Under serum-free conditions, A431 cells were treated for 24 hours with doxorubicin liposomes, which were enriched with various mol % of $C_8$-GlcCer. Doxorubicin concentrations were 0 µM (filled—empty controls) or 50 µM (hatched). Viability was assessed by MTT assay, and expressed as mean %±SD (n=3, each experiment performed in 4-fold). Untreated control cells were set at 100% viability. $C_8$-GlcCer co-formulation improves the efficacy of liposomal doxorubicin.

The in vitro efficacy of the adapted liposomes was tested by the MTT assay. This assay relies on the fact that only viable cells have the required mitochondrial metabolic capacity to convert MTT into a detectable product, whereas dead or dying cells have not (see, e.g., Carmichael et al., 1987). Compared to a control treatment (set at 100%), conventional doxorubicin-loaded PEG liposomes exhibited only modest cytotoxicity (58.4% of A431 cells was still viable after 24 hours; see FIG. 4). At increasing mol % of $C_8$-GlcCer however, this viability decreased dramatically, and strongly correlated with the observed increases in cellular doxorubicin (see FIG. 2 and FIG. 3). The increased potency of the adapted liposomes can be fully attributed to doxorubicin, since control liposomes (without doxorubicin and without $C_8$-GlcCer; without doxorubicin, but with $C_8$-GlcCer) had no significant effect on cell viability. These results were confirmed by viability assessment through phase contrast microscopy, and by determination of the amount of adherent cells after treatment (not shown).

An Alternative Preparation Procedure: Post-insertion of $C_8$-GlcCer into Caelyx®

In addition to the production of liposomes with a defined lipid composition (see Table 1), it was tested whether post-insertion of $C_8$-GlcCer into existing doxorubicin liposomes (Caelyx®) also results in improved efficacy. To this end, Caelyx® was incubated for 30 minutes in buffer supplemented with various concentrations of $C_8$-GlcCer. After washing the liposomes, TLC analysis revealed that this procedure sufficed to incorporate substantial amounts of $C_8$-GlcCer into Caelyx®, in a concentration-dependent manner (see insert of FIG. 6). However, due to the presence of the PEG shielding, it is difficult to assess on theoretical grounds, whether the lipid actually inserted into the liposomal bilayer, or merely remained associated to the liposomal surface.

Figure 6:
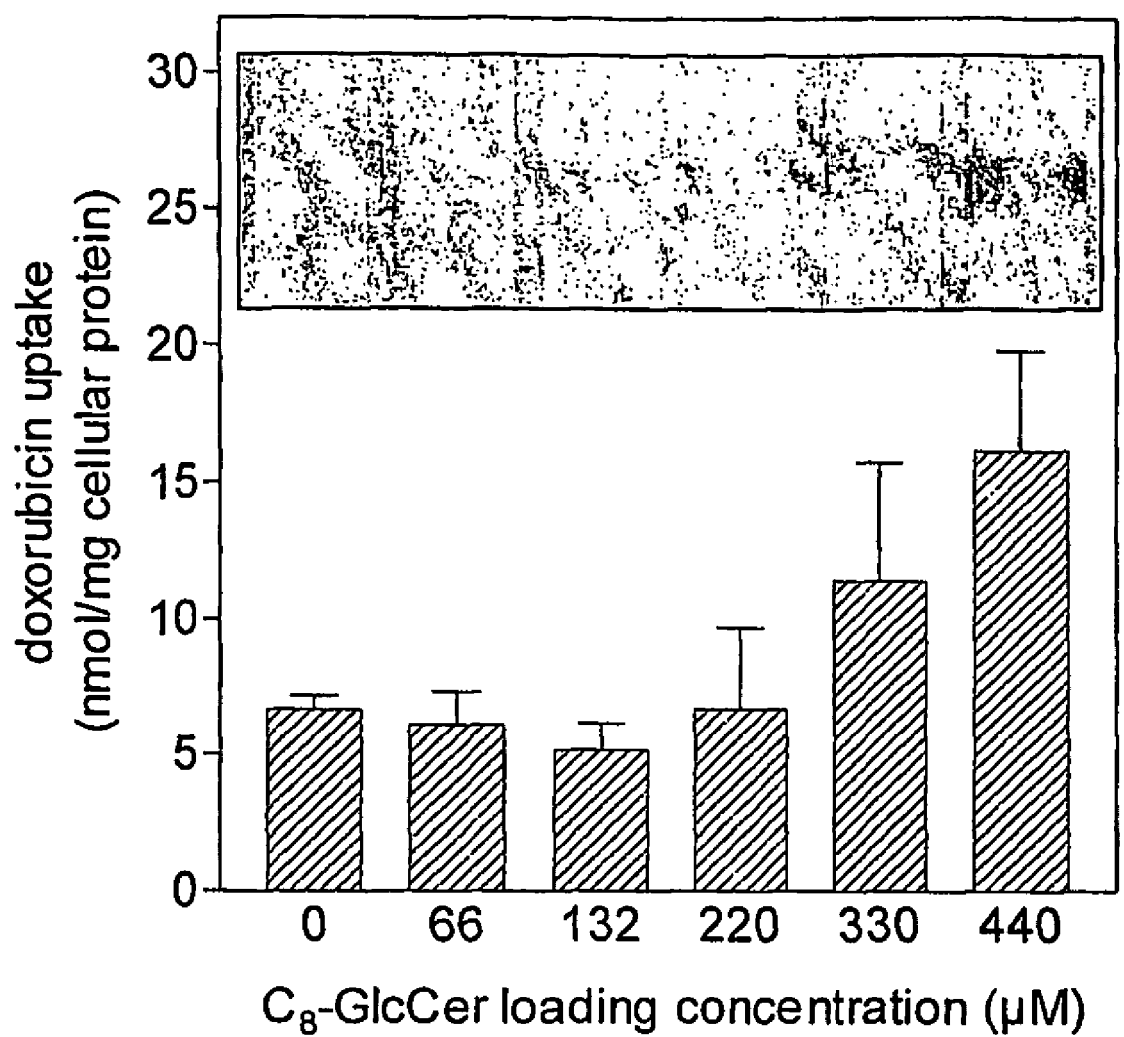
FIG. 6 is a bar-graph of doxorubicin uptake (nmol/mg cellular protein) for different loading concentrations (µM) of $C_8$-GlcCer. Commercial PEG-liposomal doxorubicin was loaded with $C_8$-GlcCer by a post-insertion procedure, using a buffer containing the indicated lipid concentrations. Insertion was confirmed by TLC analysis (see photograph above bar-graph). For 24 hours, under serum-free conditions, A431 cells were exposed to 20 µM doxorubicin, delivered as modified Caelyx®. After washing the cells, cellular doxorubicin was quantified and corrected for total cellular protein. Shown are mean results±SD (n=3). Post-insertion of $C_8$-GlcCer into Caelyx® is equally effective.

Nevertheless, $C_8$-GlcCer loading resulted in an improved doxorubicin transfer (see FIG. 6). This was reflected by an increased efficacy, as determined by the MTT viability assay: 76.2±18.2% of A431 cells were still viable after 24 hour incubation with normal Caelyx®. With post-insertion $C_8$-GlcCer-enriched Caelyx®, this decreased to 19.2±11.8%. Since liposome production involves tedious and time-consuming procedures, post-insertion thus provides a convenient alternative for quick preparation of $C_8$-GlcCer-enriched batches of liposomal doxorubicin.

$C_8$-GlcCer-enriched Liosomes are Relative Insensitive to Serum Components

Figure 5:
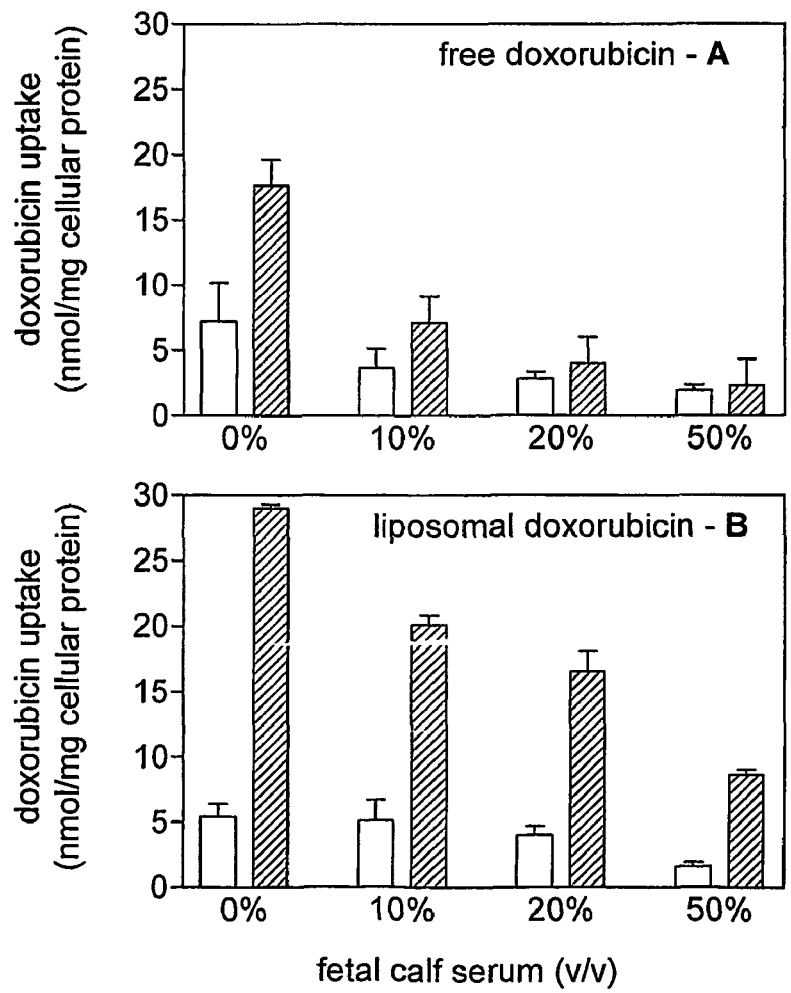
FIG. 5 is two bar-graphs of doxorubicin uptake (nmol/mg cellular protein) for different concentrations (v/v) of fetal calf serum. In the presence of various concentrations of fetal calf serum, A431 cells were treated for 24 hours with 50 µM of free doxorubicin, in the absence (open bars) or presence of 10 µM $C_8$-GlcCer (A) (hatched bars). Alternatively, cells were treated under similar conditions, but with 50 µM doxorubicin-loaded PEG-liposomes, containing either 0 mol % $C_8$-GlcCer (open bars) or 17 mol % of $C_8$-GlcCer (hatched bars) (B). (Liposomal) doxorubicin that was not taken up by the cells was washed away, and the cells were lysed. Cellular doxorubicin was then quantified and corrected for protein contents (mean±SD, n=3). $C_8$-GlcCer-enriched liposomal doxorubicin retains its efficacy in the presence of serum.

Under serum-free conditions, $C_8$-GlcCer improves the cellular uptake of free doxorubicin (see FIG. 2). However, in the presence of serum, both the uptake and the enhancing effect of the lipid hereupon, were strongly reduced (see FIG. 5A). Most likely, this is due to the high affinity of albumin and lipoproteins for amphiphilic drugs and lipids, thereby preventing interaction of these molecules with cells. Although less pronounced, the uptake of doxorubicin from conventional PEG-liposomes was also diminished by the presence of serum (see FIG. 5B). Interestingly, however, the relative effect of co-formulated $C_8$-GlcCer was fully retained under high-serum conditions. In the presence of 50% (v/v) serum for example, 8.6±0.4 nmol/mg doxorubicin was taken up from $C_8$-GlcCer-enriched liposomes, whereas this was only 1.6±0.3 nmol/mg from an equal amount of $C_8$-GlcCer-free liposomes. Comparable results were obtained with (post-inserted $C_8$-GlcCer) Caelyx® (not shown).

As expected, high serum concentrations had a strong protective effect on the viability of doxorubicin-treated A431 tumor cells. In the presence of 50% serum for example, 85.4±9.1% of all cells survived a 24 hour-treatment with conventional liposomal doxorubicin. This could be overcome, however, by employing $C_8$-GlcCer-enriched doxorubicin liposomes, which left only 35.7±6.2% of the cells viable under these conditions. Again, the increased drug uptake correlated well with an increased toxicity.

In conclusion, $C_8$-GlcCer-enriched doxorubicin liposomes (either by preparation or by post-insertion into Caelyx®) are superior both to free doxorubicin and to conventional liposomal doxorubicin (and to Caelyx®), under high serum conditions. These results indicate feasibility of in vivo applications of $C_8$-GlcCer modified liposomes. Efficacy and toxicity studies in animal tumor xenograft models are ongoing.

$C_8$-GlcCer Acts by Enhancing Cellular Uptake of Released Doxorubicin

The interaction of the modified liposomes with cultured cells was investigated further. Combined with data from the literature, this revealed a possible sequence of complex events. Due to their hydrophilic coating, PEG-liposomes are not taken up by cells, and neither do they fuse with plasma membranes (see, e.g., Koning et al., 1999, 2003; Everts et al., 2003). Instead, their doxorubicin content is gradually released into the extracellular space, from where it is then taken up by neighboring cells (see, e.g., Horowitz et al., 1992; Harasym et al., 1997). Incorporation $C_8$-GlcCer into the liposomal bilayer did not lead to enhanced doxorubicin leakage, and neither did it result in improved loading efficiencies (see Table 1). Apparently, the lipid analogue does not affect doxorubicin diffusion through the liposomal bilayer, and therefore does not enhance its release rate.

Direct transfer of the drug to the plasma membrane, via liposome-cell contact, does not occur and is not induced by $C_8$-GlcCer. This was established by experiments in which Dowex was employed, a non-toxic ion-exchange resin that binds to free doxorubicin with high affinity, but not to liposome-encapsulated doxorubicin (see, e.g., Storm et al., 1985; Druckmann et al., 1989). Supplementation of cell culture media with 5 mg/ml Dowex, which is itself not taken up by cells, prevented death of A431 cells, as induced by a 24 hour-treatment with conventional PEG-liposomal doxorubicin (90.4±24.9% of A431 cell survival, whereas only 8.7±0.8% survived in the absence of Dowex). Cell death induced by 17 mol % $C_8$-GlcCer containing liposomal doxorubicin, could also be largely prevented (81.9±6.3% in the presence of Dowex, versus 26.3±4.2% in its absence). Cellular drug delivery via the aqueous extracellular environment, rather than by direct membrane-membrane contact, also explains the sensitivity of liposomal doxorubicin towards serum (see FIG. 5B).

The inventors have demonstrated (not shown) that plasma membrane-inserted sphingolipid analogues, such as $C_8$-GlcCer, improve the uptake of free (non-liposomal) doxorubicin, by facilitating its transmembrane diffusion. This phenomenon is not observed in simple membrane systems, such as liposomes (see above), but it clearly occurs in complex biological membranes. The complex molecular and cellular mechanisms are, however, not fully understood, and are currently under investigation. Importantly, a simultaneous presence of the free drug and the lipid in the culture media was not required for the effect, and no drug-lipid complex formation was involved. In fact, a pre-incubation of cells with the sphingolipid analogue (and subsequent removal of non-cell associated lipid), sufficed to improve the cellular uptake of subsequently added doxorubicin. The present study demonstrated that when free doxorubicin was added to A431 cells that were co-treated with empty 17 mol % $C_8$-GlcCer liposomes, uptake of the agent increased 260.4±28.2%, as compared to 100% uptake in the presence of empty liposomes that omit $C_8$-GlcCer. Conversely, doxorubicin uptake from normal liposomes (0 mol % $C_8$-GlcCer) improved, when $C_8$-GlcCer was added separately, rather than co-formulated in the liposome (not shown). Taken together, these results indicate that the lipid acts at the level of the cell (membrane), and not within the liposome or the aqueous environment.

An important question concerns the way $C_8$-GlcCer reaches the plasma membrane from the liposomes. Interestingly, serum does not inhibit the relative effect of $C_8$-GlcCer on liposomal doxorubicin uptake, despite the presence of large amounts of lipid-binding proteins (see FIG. 5B). In contrast to doxorubicin therefore, the lipid analogue might (partly) relocate via direct contact between cell-associated liposomes and the plasma membrane. This common move, spontaneously performed by many short-chain lipid analogues, eventually results in an equilibrium in $C_8$-GlcCer distribution over the cells and the liposomes (see, e.g., Jeckel and Wieland, 1993; Bai and Pagano, 1997).

Without wishing to be bound by any particular theory, the inventors postulate the following sequence of events, which might explain the improved action of $C_8$-GlcCer-enriched liposomal doxorubicin. Upon addition of the liposomes, doxorubicin is gradually released into the cell culture medium, just like from normal liposomes. From those liposomes that associate to cells, $C_8$-GlcCer spontaneously crosses to the plasma membrane, whereas the other liposome components do not. Upon lateral diffusion, the lipid analogues might then create local areas within the plasma membrane that exhibit an increased susceptibility towards amphiphilic drugs. Although the details are yet unknown, this results an enhanced cellular influx and accumulation of doxorubicin, in turn explaining the improved cytotoxic action of $C_8$-GlcCer-enriched liposomes.

Additional Studies of a Range of Lipids

A range of glycosphingolipids and sphingomyelins having different structures were also studied. The data are summarised in the following tables, and are expressed as a percentage (+/−SD) of doxorubicin uptake by cultured BAEC, as compared to drug uptake in the absence of lipid. Glycosphingolipids and sphingomyelins were used at 10 μM. Doxorubicin was administered simultaneously at 50 μM. After 60 minutes, cells were washed and cellular doxorubicin contents were determined fluorimetrically. Background fluorescence was subtracted from all values and all data were corrected for protein contents. Each data point is the average value of at least three independent experiments, but some lipids were assayed in 10 or more independent experiments. For each experiment 4, 6 or 8 wells with cells were treated identically and the data were then averaged (=1 experiment).

TABLE 2

| | | | Glycosphingolipids | | | | | |
|---|---|---|---|---|---|---|---|---|
| lipid | α | $R^1$ | | $R^2$ | $R^3$ | $R^4$ | $R^5$ | $R^N$ | mean % ± SD |
| control | — | — | | — | — | — | — | — | 100.0 ± 17.0 |
| C0-GlcCer | trans | monosaccharide (glucose) | | — | $C_{13}$ | OH | H | H | 86.7 ± 16.2 |
| C8-GlcCer | trans | monosaccharide (glucose) | | $C_7$ | $C_{13}$ | OH | H | H | 335.8 ± 88.5 |
| C12-GlcCer | trans | monosaccharide (glucose) | | $C_{11}$ | $C_{13}$ | OH | H | H | 85.6 ± 12.0 |
| C0-GalCer | trans | monosaccharide (galactose) | | — | $C_{13}$ | OH | H | H | 98.2 ± 9.3 |
| C8-GalCer | trans | monosaccharide (galactose) | | $C_7$ | $C_{13}$ | OH | H | H | 213.7 ± 31.1 |
| C0-LacCer | trans | disaccharide (glucose + galactose) | | — | $C_{13}$ | OH | H | H | 93.8 ± 4.0 |
| C8-LacCer | trans | disaccharide (glucose + galactose) | | $C_7$ | $C_{13}$ | OH | H | H | 301.5 ± 41.2 |
| ganglioside mix | trans | oligosaccharides (mixture) | | $C_{15}$-$C_{23}$ | $C_{13}$ | OH | H | H | 130.7 ± 14.3 |

TABLE 3

| | | | Sphingomyelins | | | | | |
|---|---|---|---|---|---|---|---|---|
| lipid | α | $R^1$ | $R^2$ | $R^3$ | $R^4$ | $R^5$ | $R^N$ | mean % ± SD |
| sphingosine | trans | —OH | — | $C_{13}$ | OH | H | H | 100.4 ± 20.3 |
| C6-Cer | trans | —OH | $C_5$ | $C_{13}$ | OH | H | H | 96.6 ± 17.3 |
| C8-Cer-1-P | trans | phosphate | $C_7$ | $C_{13}$ | OH | H | H | 122.2 ± 7.2 |
| natural SM | trans | phosphocholine | $C_{15}$-$C_{23}$ | $C_{13}$ | OH | H | H | 91.1 ± 18.2 |
| C0-SM (SPC) | trans | phosphocholine | — | $C_{13}$ | OH | H | H | 128.3 ± 19.5 |
| C2-SM | trans | phosphocholine | $C_1$ | $C_{13}$ | OH | H | H | 128.9 ± 6.4 |
| C6-SM | trans | phosphocholine | $C_5$ | $C_{13}$ | OH | H | H | 330.6 ± 92.3 |
| 3-O-methyl-C8-SM | trans | phosphocholine | $C_7$ | $C_{13}$ | O—Me | H | H | 249.8 ± 36.5 |

The foregoing has described the principles, preferred embodiments, and modes of operation of the present invention. However, the invention should not be construed as limited to the particular embodiments discussed; Instead, the above-described embodiments should be regarded as illustrative rather than restrictive, and it should be appreciated that variations may be made in those embodiments by workers skilled in the art without departing from the scope of the present invention.

REFERENCES

A number of patents and publications are cited above in order to more fully describe and disclose the invention and the state of the art to which the invention pertains. Full citations for these references are provided below. Each of these references is incorporated herein by reference in its entirety into the present disclosure, to the same extent as if each individual reference was specifically and individually indicated to be incorporated by reference.

Abraham S A, Edwards K, Karlsson G, Macintosh S, Mayer L D, McKenzie C, Bally M B, 2002, "Formation of transition metal-doxorubicin complexes inside liposomes," Biochim. Biophys. Acta., Vol. 1565(1), pp. 41-54.

Allen et al., 1996, "Solid-Tumor Treatment Method," U.S. Pat. No. 5,527,528 granted 18 Jun. 1996.

Bai J, Pagano R E, 1997, "Measurement of spontaneous transfer and transbilayer movement of BODIPY-labeled lipids in lipid vesicles," Biochemistry, Vol. 34, pp. 8840-8848.

Bligh E J, Dyer W J, 1959, "A rapid method of total lipid extraction and purification," Can. J. Biochem. Physiol., Vol. 37, pp. 911-917.

Carmichael J, DeGraff W G, Gazdar A F, Minna J D, Mitchell J B, 1987, "Evaluation of a tetrazolium-based semiautomated colorimetric assay: assessment of chemosensitivity testing," Cancer Res., Vol. 47, pp. 936-942.

Cheung B C, Sun T H, Leenhouts J M, Cullis P R, 1998, "Loading of doxorubicin into liposomes by forming Mn2+-drug complexes," Biochim. Biophys. Acta., Vol. 1414(1-2), pp. 205-216.

Denichi, Mizuno, et al., 1996, "Carriers for Medicines Composed of Sphingoglycolipids Micelles—Prepared by the Addition of Solution of Medicinal Compounds to Micelles," Japanese patent publication number JP 8-034746 published 6 Feb. 1996.

Druckmann S, Gabizon A, Barenholz Y, 1989, "Separation of liposome-associated doxorubicin from non-liposome-associated doxorubicin in human plasma: implications for pharmacokinetic studies," Biochim. Biophys. Acta, Vol. 980, pp. 381-384.

Everts M, Koning G A, Kok R J, Asgeirsdottir S A, Vestweber D, Meijer D K, Storm G, Molema G, 2003, "In vitro cellular handling and in vivo targeting of E-selectin-directed immunoconjugates and immunoliposomes used for drug delivery to inflamed endothelium," Pharm. Res., Vol. 20, pp. 64-72.

Gabizon A, 2001, "Pegylated liposomal doxorubicin: metamorphosis of an old drug into a new form of chemotherapy," Cancer Inv., Vol. 19, pp. 424-436.

Gabizon A, Chemia M, Tzemach D, Horowitz A T, Goren D, 1996, "Liposome longevity and stability in circulation: effects on the in vivo delivery to tumors and therapeutic efficacy of encapsulated anthracyclines," J. Drug Target, Vol. 3, pp. 391-398.

Ghidoni R, Sala G, Giuliani A, 1999, "Use of sphingolipid analogs: benefits and risks," Biochim. Biophys. Acta, Vol. 1439, pp. 17-39.

Haran G, Cohen R, Bar L K, Barenholz Y, 1993, "Transmembrane ammonium sulphate gradients in liposomes produce efficient and stable entrapment of amphipathic weak bases," Biochim. Biophys. Acta, Vol. 1151, pp. 201-215.

Harasym T O, Cullis P R, Bally M B, 1997, "Intratumor distribution of doxorubicin following i.v. administration of drug encapsulated in egg phsophatidylcholine/cholesterol liposomes," Cancer Chemother. Pharmacol., Vol. 40, pp. 309-317.

Heijn M, Roberge S, Jain R K, 1999, "Cellular membrane permeability of anthracyclines does not correlate with their delivery in a tissue-isolated tumor," Cancer Res., Vol. 59, pp. 4458-4463.

Hellmann, K., 1988, "Pharmaceutical Compositions for the Treatment of Cancers," published international (PCT) patent application publication number WO 88/01171, published 25 Feb. 1988.

Horowitz A T, Barenholz Y, Gabizon A, 1992, "In vitro cytotoxicity of liposome-encapsulated doxrubicin: dependence on liposome composition and drug release," Biochim. Biophys. Acta, Vol. 1109, pp. 203-209.

Jeckel D, Wieland F, 1993, "Truncated ceramide analogs as probes for sphingolipid biosynthesis and transport," Adv. Lipid Res., Vol. 26, pp. 143-160.

Koning G A, Gorter A, Scherphof G L, Kamps J A A M, 1999, "Antiproliferative effect of immunoliposomes containing 5-fluorodeoxyuridine-dipalmitate on colon cancer cells," Br. J. Cancer, Vol. 80, pp. 1718-1725.

Koning G A, Morselt H W M, Gorter A, Allen T M, Zalipsky S, Scherphof G L, Kamps J A A M, 2003, "Interaction of differently designed immunoliposomes with colon cancer cells and kupffer Cells. An in vitro comparison," Pharm. Res., Vol. 20, pp. 1249-1258.

Koning, G. A., Veldman, R. J., van Hell, A., Zerp, S., Storm, G., van Blitterswijk, W. J., Verheij, M., 2003, "Short-chain liposomal sphingolipids potentiate in vitro doxorubicin cytotoxicity by enhancing its cellualr influx," Conference Abstract for Liposome Advances: Progress in Drug and Vaccine Delivery, 15-19 Dec. 2003, London, UK.

Lasic D D, Ceh B, Stuart M C, Guo L, Frederik P M, Barenholz Y, 1995, "Transmembrane gradient driven phase transitions within vesicles: lessons for drug delivery," *Biochim. Biophys. Acta.*, Vol. 1239(2), pp. 145-156.

Liotta, D., et al., 1999, "Sphingolipid Derivatives and Their Methods of Use," published international (PCT) patent application publication number WO 99/41266 published 19 Aug. 1999.

Lothstein L, Israel M, Sweatman T W, 2001, "Anthracyclin drug targeting: cytoplasmic versus nuclear—a fork in the road," *Drug Res. Updates*, Vol. 4, pp. 169-177.

Mabray, S., et al., 1978, Biochem., Vol. 17, pp. 2464-2468.

Martin, F. J., 1990, in: *Specialized Drug Delivery Systems—Manufacturing and Production Technology* (P. Tyle, ed.) (Marcel Dekker, New York, publisher), pp. 267-316.

Martin, F. J., et al., 1993, "Solid Tumor Treatment Method and Composition," U.S. Pat. No. 5,213,804, granted 25 May 1993.

Mayer, L. D., et al., 1986, *Biochim. Biophys. Acta*, Vol. 857, pp. 123-126.

Mayer, L. D., et al., 1989, *Cancer Res.*, Vol. 49, pp. 5922-5930.

Olson, F., et al., 1979, *Biochim. Biophys. Acta*, Vol. 557, pp. 9-23.

Pan X Q, Wang H, Lee R J, 2003, "Antitumor activity of folate receptor-targeted liposomal doxorubcin in a KB oral carcinoma murine xenograft model," *Pharm. Res.*, Vol. 20, pp. 417-422.

Park J W, Hong K, Kirpotin D B, Colbern G, Shalaby R, Baselga J, Shao Y, Nielsen U B, Marks J D, Moore D, Papahadjopoulos D, Benz C C, 2002, "Anti-Herb 2 immunoliposomes: enhanced efficacy attributable to targeted delivery," *Clin. Cancer Res.*, Vol. 8, pp. 1172-1181.

Robert J, Gianni L, 1993, "Pharmacokinetics and metabolism of anthracyclines," in Cancer Surveys 17 (Workman P and Graham M A, eds), pp. 219-252.

Rouser G, Fkeischer S, Yamamoto A, 1970, "Two-dimensional thin layer chromatographic separation of polar lipids and determination of phospholipids by phosphorus analysis of spots," *Lipids*, Vol. 5, pp. 494-496.

Smith P K, Krohn R I, Hermanson G T, Mallia A K, Gartner F H, Provenzano M D, Fujimotot E K, Goeke N M, Olson B J, Klenk D C, 1985, "Measurement of protein using bicinchoninic acid," *Anal. Chem.*, Vol. 150, pp. 76-85.

Speth P A, Raijmakers R A, Boezeman J B, Linssen P C, de Witte T J, Wessels H M, Haanen C, 1988, "In vivo cellular adriamycin concentrations related to growth inhibition of normal and leukemic human bone marrow cells," *Eur. J. Cancer Clin. Oncol.*, Vol. 24, pp. 667-674.

Storm G, van Bloois L, Brouwer M, Crommelin D J A, 1985, "The interaction of cytostatic drugs with adsorbents in aqueous media," *Biochim. Biophys. Acta*, Vol. 818, pp. 343-351.

Szoka, F., Jr., et al., 1980, *Ann. Rev. Biophys. Biogen.*, Vol. 9, p. 457.

Tardi P G, Boman N L, Cullis P R, 1996, "Liposomal doxorubicin," *J. Drug Target*, Vol. 4, pp. 129-140.

Tsong, T. Y., 1975, Biochem., Vol. 14, pp. 5409-5414; pp. 5415-5417.

Tubaro, E., et al., 1995, "Effect of a new de-N-acetyl-lysoglycosphingolipid on some tumour models," *European Journal of Pharmacology*, Vol. 294, pp. 555-563.

Uster P S, Allen T M, Daniel B E, Mendez C J, Newman M S, Zhu G Z, 1996, "Insertion of poly(ethylene glycol) derivatized phospholipid into pre-fromed liposomes results in prolonged in vivo circulation time," *FEBS Lett.*, Vol. 386, pp. 243-246.

Vaage J, Mayhew E, Lasic D, Martin F, 1992, "Therapy of primary and metastatic mouse mammary carcinomas with doxorubicin encapsulated in long circulating liposomes," *Int. J. Cancer*, Vol. 51, pp. 942-948.

Veldman, R. J., Zerp, S., van Blitterwijk, W. J., Verheij, M., 2004, "N-hexanoyl-sphingomyelin potentiates in vitro doxorubicin cytotoxicity by enhancing its cellular influx," *British Journal of Cancer*, Vol. 90, pp. 917-925.

Verheij, M., Veldman, R. J., Zerp, S., van Blitterswijk, W. J., 2003, "N-hexanoyl-sphingomyelin potentiates in vitro doxorubicin cytotoxicity by enhancing its cellular influx," Conference Abstract #C228 for MCR-NCI-EORTC International Conference on Molecular Targets and Cancer Therapeutics, 17-21 Nov. 2003, Boston, Mass., USA.

Washington N, Washington C, Wilson C G, 2001, "Cell membranes, epithelial barriers and drug absorption," in *Physiological Pharmaceutics: Barriers to Drug Absorption*, pp. 1-18, (publishers: Taylor and Francis: London).

Weiss R B, 1992, "The anthracyclines: will we ever find a better doxorubicin?", *Sem. Oncol.*, Vol. 19, pp. 670-686.

Woodle et al., 1991, "Liposomes with Enhanced Circulation Time," U.S. Pat. No. 5,013,556.

Yuan F. Leunig M, Huang S K, Berk D A, Papahadjopoulos D, Jain R K, 1994, "Microvascular permeability and interstitial penetration of sterically stabilized (stealth) liposomes in a human tumor xenograft," *Cancer Res.*, Vol. 54, pp. 3352-3356.

Zagotto G, Gatto B, Moro S, Siss C, Palumbo M, 2001, "Anthracyclins: recent developments in their separation and quantitation," *J. Chromat. B*, Vol. 764, pp. 161-171.

Zalipsky et al., 1995, "Lipid-Polymer Conjugates and Liposomes," U.S. Pat. No. 5,395,619 granted 7 Mar. 1995.

The invention claimed is:

1. A pharmaceutical formulation suitable for parenteral administration comprising:
   (i) an amphiphilic drug selected from the group consisting of an anthracycline and an alkaloid; and
   (ii) a short-chain sphingolipid selected from compounds of the following formula:

$$\underset{R^4}{\overset{R^N}{\underset{|}{N}}}\underset{}{\overset{O}{\underset{}{\|}}}\underset{}{\overset{}{}}$$

wherein:
$R^1$ is independently:
   an O-linked saccharide group; or
   an O-linked polyhydric alcohol group;
or:
$R^1$ is independently:
   an O-linked (optionally N—($C_{1-4}$alkyl)-substituted amino)-$C_{1-6}$alkyl-phosphate group; or
   an O-linked (polyhydric alcohol-substituted)-$C_{1-6}$alkyl-phosphate group;
$R^2$ is independently $C_{3-9}$alkyl,
   and is independently unsubstituted or substituted;

$R^3$ is independently $C_{7-19}$alkyl,
and is independently unsubstituted or substituted;
$R^4$ is independently —H, —OH, or —O—$C_{1-4}$alkyl;
$R^N$ is independently —H or $C_{1-4}$alkyl;
the bond marked with an alpha (α) is independently a single bond or a double bond;
if the bond marked with an alpha (α) is a double bond, then $R^5$ is —H;
if the bond marked with an alpha (α) is a single bond, then $R^5$ is —H or —OH;
the carbon atom marked (*) is independently in an R-configuration or an S-configuration;
the carbon atom marked (**) is independently in an R-configuration or an S-configuration;
with the proviso that when $R^1$ is an O-linked saccharide group which is derived from galactopyranose, then $R^1$ is D-galactopyranosyl-β1-;
and pharmaceutically acceptable salts thereof.

2. A pharmaceutical formulation according to claim 1, wherein said drug is an anthracycline.

3. A pharmaceutical formulation according to claim 1, wherein said drug is selected from: doxorubicin, idarubicin, epirubicin, aclarubicin, mitrozantrone, and daunorubicin, and salts thereof.

4. A pharmaceutical formulation according to claim 1, wherein said drug is doxorubicin or doxorubicin hydrochloride.

5. A pharmaceutical formulation according to claim 1, wherein said drug is an alkaloid.

6. A pharmaceutical formulation according to claim 1, wherein said drug is selected from: topotecan and camptothecin.

7. A pharmaceutical formulation according to claim 1, wherein $R^2$ is linear.

8. A pharmaceutical formulation according to claim 1, wherein $R^2$ is linear; and has from 0 to 3 carbon-carbon double bonds.

9. A pharmaceutical formulation according to claim 1, wherein $R^2$ is unsubstituted or substituted with from 1 to 3 substituents selected from $C_{1-4}$alkyl, —OH, $C_{1-4}$alkoxy, —C(=O)OH, and —C(=O)O—$C_{1-4}$alkyl.

10. A pharmaceutical formulation according to claim 1, wherein $R^2$ is —$(CH_2)_n CH_3$, wherein n is an integer from 4 to 8.

11. A pharmaceutical formulation according to claim 1, wherein $R^2$ is —$(CH_2)_n CH_3$, wherein n is an integer from 6 to 8.

12. A pharmaceutical formulation according to claim 1, wherein $R^2$ is —$(CH_2)_6 CH_3$.

13. A pharmaceutical formulation according to claim 1, wherein the bond marked alpha is a double bond and $R^5$ is —H.

14. A pharmaceutical formulation according to claim 1, wherein the bond marked alpha is a single bond; and $R^5$ is —H.

15. A pharmaceutical formulation according to claim 1, wherein the bond marked alpha is a single bond; and $R^5$ is —OH.

16. A pharmaceutical formulation according to claim 1, wherein $R^3$ is linear.

17. A pharmaceutical formulation according to claim 1, wherein $R^3$ is linear; and has from 0 to 3 carbon-carbon double bonds.

18. A pharmaceutical formulation according to claim 1, wherein $R^3$ is unsubstituted or substituted with from 1 to 3 substituents selected from $C_{1-4}$alkyl, —OH, $C_{1-4}$alkoxy.

19. A pharmaceutical formulation according to claim 1, wherein $R^3$ is —$(CH_2)_n CH_3$, wherein n is an integer from 8 to 16.

20. A pharmaceutical formulation according to claim 1, wherein $R^3$ is —$(CH_2)_{12} CH_3$.

21. A pharmaceutical formulation according to claim 1, wherein the moiety:

is selected from the following:
—$(CH_2)_8$—$CH_3$;
—$(CH_2)_{10}$—$CH_3$;
—$(CH_2)_{12}$—$CH_3$;
—$(CH_2)_{14}$—$CH_3$;
—$(CH_2)_7$—CH=CH—$(CH_2)_5$—$CH_3$;
—$(CH_2)_{16}$—$CH_3$;
—$(CH_2)_7$—CH=CH—$(CH_2)_7$—$CH_3$;
—$(CH_2)_9$—CH=CH—$(CH_2)_5$—$CH_3$;
—$(CH_2)_7$—[CH=CH—$CH_2$]$_2$—$(CH_2)_3$—$CH_3$;
—$(CH_2)_7$—[CH=CH—$CH_2$]$_3$—$CH_3$;
—$(CH_2)_4$—[CH=CH—$CH_2$]$_3$—$(CH_2)_3$—$CH_3$;
—$(CH_2)_7$—[CH=CH]$_3$—$(CH_2)_3$—$CH_3$;
—$(CH_2)_{18}$—$CH_3$;
—$(CH_2)_6$—[CH=CH—$CH_2$]$_2$—$(CH_2)_6$—$CH_3$;
—$(CH_2)_3$—[CH=CH—$CH_2$]$_3$—$(CH_2)_6$—$CH_3$;
—$(CH_2)_3$—[CH=CH—$CH_2$]$_4$—$(CH_2)_3$—$CH_3$;
—$(CH_2)_{20}$—$CH_3$;
analogs of the foregoing wherein the left-most —$(CH_2)_2$— is replaced with —CH=CH—; and
analogs of the foregoing wherein the left-most —$(CH_2)$— is replaced with —CH(OH)—.

22. A pharmaceutical formulation according to claim 1, wherein $R^4$ is —H, —OH, —OMe, —OEt, —O(iPr), —O(nPr), —O(nBu), —O(iBu), —O(sBu), or —O(tBu).

23. A pharmaceutical formulation according to claim 1, wherein $R^4$ is —OH.

24. A pharmaceutical formulation according to claim 1, wherein $R^N$ is —H, -Me, or -Et.

25. A pharmaceutical formulation according to claim 1, wherein the carbon atoms marked (*) and (**) have a configuration as shown in the following formula:

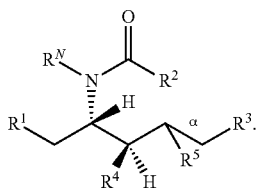

26. A pharmaceutical formulation according to claim 1, wherein $R^1$ is an O-linked saccharide group.

27. A pharmaceutical formulation according to claim 1, wherein $R^1$ is an O-linked mono-, di-, or tri-saccharide group.

28. A pharmaceutical formulation according to claim 1, wherein $R^1$ is comprises a group or groups selected from:
   arabinose, lyxose, ribose, xylose,
   allose, altrose, glucose, mannose, gulose, idose, galactose, and talose;
   and derivatives thereof.

29. A pharmaceutical formulation according to claim 1, wherein $R^1$ is an O-linked mono-, di-, or tri-saccharide group comprising a group or groups selected from:
   arabinose, lyxose, ribose, xylose,
   allose, altrose, glucose, mannose, gulose, idose, galactose, talose,
   sucrose, maltose, lactose, cellobiose, galabiose,
   globotriaose, isoglobotriaose, mucotriaose, lactotriaose, neolactotriaose gangliotriaose, galatriaose, mollutriaose, and antrotriaose;
   and derivatives thereof.

30. A pharmaceutical formulation according to claim 28, wherein said saccharide group derivatives are selected from deoxy, di-deoxy, di-deoxy-di-dehydro, methoxy, acetoxy, carboxylic acid, sulfuric acid, amino-deoxy, N-acetyl-amino-deoxy, or N-sulfo-amino-deoxy.

31. A pharmaceutical formulation according to claim 1, wherein said short-chain sphingolipid has the following formula ($C_8$-GlcCer):

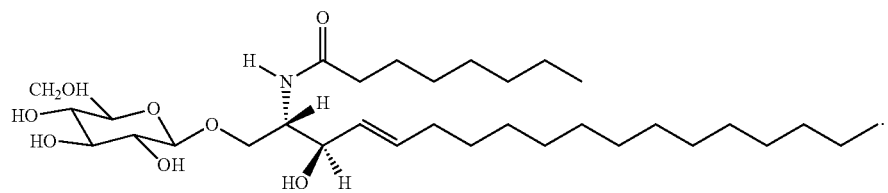

32. A pharmaceutical formulation according to claim 1, wherein said short-chain sphingolipid has the following formula:

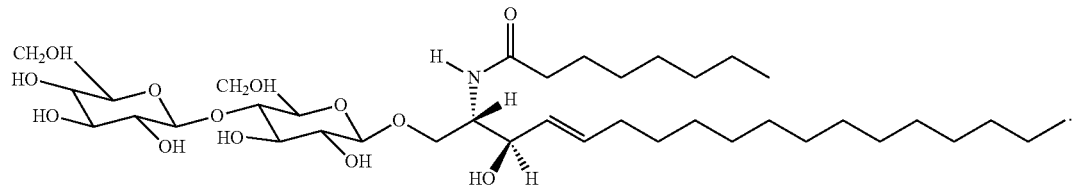

33. A pharmaceutical formulation comprising:
   (i) a drug; and
   (ii) a short-chain sphingolipids selected from compounds of the following formula

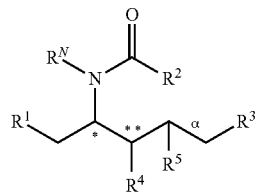

wherein:
$R^1$ is independently an O-linked polyhydric alcohol group
$R^2$ is independently $C_{3-9}$alkyl,
and is independently unsubstituted or substituted;
$R^3$ is independently $C_{7-19}$alkyl,
and is independently unsubstituted or substituted;
$R^4$ is independently —H, —OH, or —O—$C_{1-4}$alkyl;
$R^N$ is independently —H or $C_{1-4}$alkyl;
the bond marked with an alpha (α) is independently a single bond or a double bond;
if the bond marked with an alpha (α) is a double bond, then $R^5$ is —H;
if the bond marked with an alpha (α) is a single bond, then $R^5$ is —H or —OH;
the carbon atom marked (*) is independently in an R-configuration or an S-configuration;
the carbon atom marked (**) is independently in an R-configuration or an S-configuration;
and pharmaceutically acceptable salts thereof.

34. A pharmaceutical formulation according to claim 33, wherein $R^1$ comprises a group selected from: ethanediol (glycol), propanediol, butanediol, glycerol, and erythritol.

35. A pharmaceutical formulation according to claim 1, wherein $R^1$ is:
- an O-linked (optionally N—($C_{1-4}$alkyl)-substituted amino)-$C_{1-6}$alkyl-phosphate group; or
- an O-linked (polyhydric alcohol-substituted)-$C_{1-6}$alkyl-phosphate group.

36. A pharmaceutical formulation according to claim 1, wherein $R^1$ is:

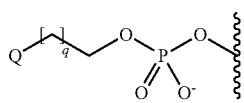

wherein:
q is an integer from 0 to 5;
Q is: —$NH_2$, —$NHR^a$, —$NR^a_2$, or —$NR^a_3{}^+$; or:
Q is a polyhydric alcohol group, linked via an oxygen atom;
each $R^a$ is linear or branched saturated $C_{1-4}$alkyl.

37. A pharmaceutical formulation according to claim 1, wherein $R^1$ is:

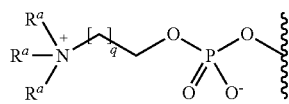

wherein:
q is an integer from 0 to 5; and
each $R^a$ is a $C_{1-4}$alkyl group.

38. A pharmaceutical formulation according to claim 1, wherein $R^1$ is:

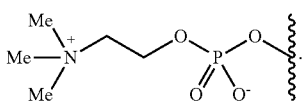

39. A pharmaceutical formulation according to claim 1, wherein said short-chain sphingolipid has the following formula ("$C_6$—SM"):

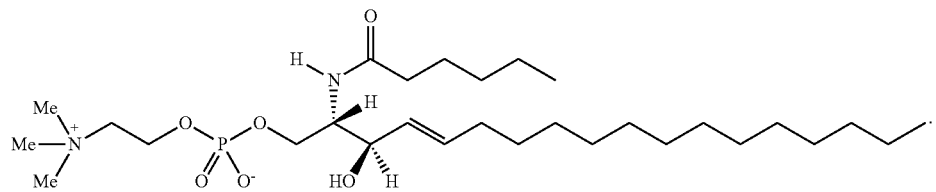

40. A pharmaceutical formulation according to claim 1, wherein said short-chain sphingolipid has the following formula ("3-O-methyl-$C_8$—SM"):

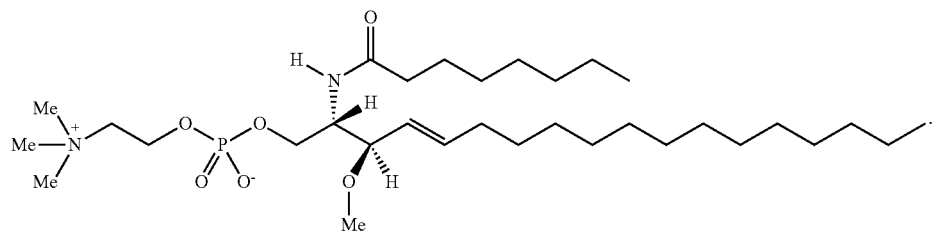

41. A pharmaceutical formulation according to claim 36, wherein Q is a polyhydric alcohol group, linked via an oxygen atom.

42. A pharmaceutical formulation according to claim 41, wherein Q comprises a group selected from: ethanediol (glycol), propanediol, butanediol, glycerol, and erythritol.

43. A pharmaceutical formulation according to claim 1, wherein the pharmaceutical formulation is a liposomal pharmaceutical formulation.

44. A liposomal pharmaceutical formulation according to claim 43, wherein the liposomes of the liposomal pharmaceutical formulation are prepared using a mixture of lipids comprising, at least, vesicle-forming lipids and said short-chain sphingolipid.

45. A liposomal pharmaceutical formulation according to claim 44, wherein said mixture of lipids comprises phospholipids and said short-chain sphingolipid.

46. A liposomal pharmaceutical formulation according to claim 44, wherein said mixture of lipids comprises phospholipids, cholesterol, and said short-chain sphingolipid.

47. A liposomal pharmaceutical formulation according to claim 44, wherein said mixture of lipids comprises phosphatidylcholines, cholesterol, and said short-chain sphingolipid.

48. A liposomal pharmaceutical formulation according to claim 44, wherein said mixture of lipids comprises fully hydrogenated soy phosphatidylcholine (HSPC), cholesterol, and said short-chain sphingolipid.

49. A liposomal pharmaceutical formulation according to claim 44, wherein said mixture of lipids comprises dipalmitoyl-phosphatidylcholine (DPPC), cholesterol, and said short-chain sphingolipid.

50. A liposomal pharmaceutical formulation according to claim 44, wherein said mixture of lipids additionally comprises a vesicle-forming lipid which is derivatized with a polymer chain.

51. A liposomal pharmaceutical formulation according to claim 44, wherein said mixture of lipids additionally comprises a phosphatidylethanolamine (PE) which is derivatized with polyethyleneglycol (PEG).

52. A liposomal pharmaceutical formulation according to claim 44, wherein said mixture of lipids additionally comprises N-(carbonyl-methoxypolyethylene glycol 2000)-1,2-distearoyl-sn-glycero-3-phosphoethanolamine sodium salt (MPEG2000-DSPE).

53. A pharmaceutical formulation according to claim 1, in the form of Caelyx® or Doxil® liposomes post-inserted with a short-chain sphingolipid selected from compounds of the following formula:

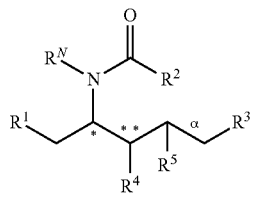

wherein:
R$^1$ is independently:
    an O-linked saccharide group; or
    an O-linked polyhydric alcohol group;
    or:
R$^1$ is independently:
    an O-linked (optionally N—(C$_{1-4}$alkyl)-substituted amino)-C$_{1-6}$alkyl-phosphate group; or
    an O-linked (polyhydric alcohol-substituted)-C$_{1-6}$alkyl-phosphate group;
R$^2$ is independently C$_{3-9}$alkyl,
    and is independently unsubstituted or substituted;
R$^3$ is independently C$_{7-19}$alkyl,
    and is independently unsubstituted or substituted;
R$^4$ is independently —H, —OH, or —O—C$_{1-4}$alkyl;
R$^N$ is independently —H or C$_{1-4}$alkyl;
    the bond marked with an alpha (α) is independently a single bond or a double bond;
    if the bond marked with an alpha (α) is a double bond, then R$^5$ is —H;
    if the bond marked with an alpha (α) is a single bond, then R$^5$ is —H or —OH;
    the carbon atom marked (*) is independently in an R-configuration or an S-configuration;
    the carbon atom marked (**) is independently in an R-configuration or an S-configuration;
with the proviso that when R$^1$ is an O-linked saccharide group which is derived from galactopyranose, then R$^1$ is D-galactopyranosyl-β1-;
and pharmaceutically acceptable salts thereof.

54. A pharmaceutical formulation suitable for parenteral administration comprising:
    (i) a drug; and
    (ii) a short-chain sphingolipid selected from compounds of the following formula:

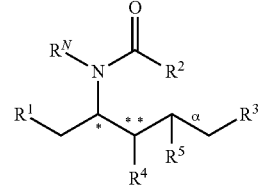

wherein:
R$^1$ is independently an O-linked polyhydric alcohol group;
R$^2$ is independently C$_{3-9}$alkyl,
    and is independently unsubstituted or substituted;
R$^3$ is independently C$_{7-19}$alkyl,
    and is independently unsubstituted or substituted;
R$^4$ is independently —H, —OH, or —O—C$_{1-4}$alkyl;
R$^N$ is independently —H or C$_{1-4}$alkyl;
the bond marked with an alpha (α) is a single bond;
R$^5$ is —H or —OH;
the carbon atom marked (*) is independently in an R-configuration or an S-configuration;
the carbon atom marked (**) is independently in an R-configuration or an S-configuration;
and pharmaceutically acceptable salts thereof.

55. A pharmaceutical formulation suitable for parenteral administration comprising:
    (i) an amphiphilic drug; and
    (ii) a short-chain sphingolipid having the following formula ("3-O-methyl-C$_8$—SM"):

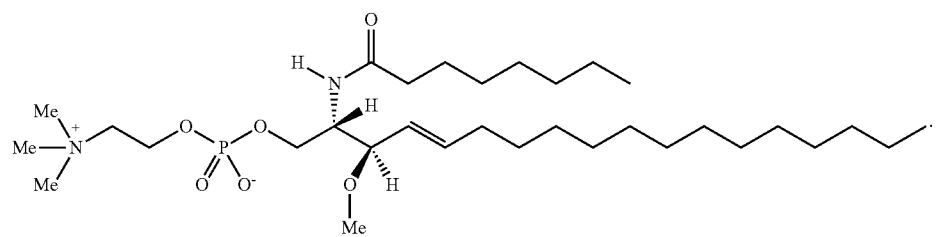
* * * * *